US012673206B2

(12) United States Patent
Seshan et al.

(10) Patent No.: US 12,673,206 B2
(45) Date of Patent: Jul. 7, 2026

(54) SPINAL CORD STIMULATOR ELECTRODE POSITIONING SYSTEM UTILIZING AN ALGORITHM FOR FILTERING ELECTROMYOGRAPHY DATA

(71) Applicant: SPINESTIM NM LLC, White Plains, NY (US)

(72) Inventors: Karthik Seshan, Ossining, NY (US); Craig Crookston, East Amherst, NY (US); Rahul Gole, Plainsboro, NJ (US); Jeremy Bamford, Mandeville, LA (US); Chris Martin, Ayer, MA (US)

(73) Assignee: SpineStim NM LLC, Ossining, NY (US)

( * ) Notice: Subject to any disclaimer, the term of this patent is extended or adjusted under 35 U.S.C. 154(b) by 908 days.

(21) Appl. No.: 17/723,315

(22) Filed: Apr. 18, 2022

(65) Prior Publication Data

US 2022/0330878 A1     Oct. 20, 2022

Related U.S. Application Data

(60) Provisional application No. 63/175,944, filed on Apr. 16, 2021.

(51) Int. Cl.
*A61B 5/313* (2021.01)
*A61B 5/00* (2006.01)
(Continued)

(52) U.S. Cl.
CPC .......... *A61N 1/36062* (2017.08); *A61B 5/313* (2021.01); *A61B 5/395* (2021.01); *A61B 5/397* (2021.01); *A61B 5/7203* (2013.01); *A61B*

5/7225 (2013.01); *A61B 5/7425* (2013.01); *A61N 1/0551* (2013.01); *A61N 1/36071* (2013.01); *A61N 1/37241* (2013.01); *A61B 5/407* (2013.01); *A61N 1/36157* (2013.01); *A61N 1/36175* (2013.01)

(58) Field of Classification Search
CPC .... A61N 1/36062; A61N 1/0551; A61B 5/40; A61B 5/407; A61B 5/4076; A61B 5/7264; A61B 5/7225; A61B 5/7228
See application file for complete search history.

(56) References Cited

U.S. PATENT DOCUMENTS 6,466,817 B1     10/2002     Kaula et al.
7,470,236 B1     12/2008     Kelleher et al.
(Continued)

*Primary Examiner* — Alyssa M Alter
(74) *Attorney, Agent, or Firm* — Caldwell LLC

(57) ABSTRACT

A spinal cord stimulator (SCS) system and method for placing SCS electrodes in a patient for spinal cord stimulation therapy. The SCS system comprises a stimulator and an amplifier unit. The amplifier unit comprises an algorithm module to store and process algorithms for processing data received from recording electrodes placed in a patient's body. The recording electrodes send real-time electromyography (EMG) data related to the patient to the algorithm module. The algorithm module processes the real-time EMG data, including filtering the EMG data to remove artifacts generated by the SCS electrodes. The SCS system compares the filtered EMG data in real-time with the pre-clinical EMG data and displays the comparison data on the display device. The displayed data is used, by the surgeon, for lateralization of the SCS electrode.

19 Claims, 16 Drawing Sheets

(51) Int. Cl.

| | |
|---|---|
| *A61B 5/395* | (2021.01) |
| *A61B 5/397* | (2021.01) |
| *A61N 1/05* | (2006.01) |
| *A61N 1/36* | (2006.01) |
| *A61N 1/372* | (2006.01) |

(56) References Cited

U.S. PATENT DOCUMENTS

| | | | |
|---|---|---|---|
| 7,522,953 B2 | 4/2009 | Kaula et al. | |
| 8,303,516 B2 | 11/2012 | Schmitz et al. | |
| 8,562,539 B2 | 10/2013 | Marino | |
| 8,801,626 B2 | 8/2014 | Sun et al. | |
| 8,996,123 B2 | 3/2015 | Goetz et al. | |
| 9,392,953 B1 | 7/2016 | Gharib | |
| 10,258,798 B2 | 4/2019 | Panken et al. | |
| 10,406,369 B2 | 9/2019 | Jiang et al. | |
| 10,660,567 B2 | 5/2020 | Cadwell | |
| 10,716,509 B2 | 7/2020 | Kaula et al. | |
| 10,814,134 B2 | 10/2020 | Serrano Carmona et al. | |
| 10,912,944 B2 | 2/2021 | Serrano Carmona et al. | |
| 11,026,627 B2 | 6/2021 | Scott et al. | |
| 11,497,916 B2 | 11/2022 | Jiang et al. | |
| 11,648,401 B2 | 5/2023 | O'Brien et al. | |
| 2015/0073306 A1* | 3/2015 | Abeyratne | G16H 50/30 |
| | | | 600/586 |
| 2018/0193651 A1* | 7/2018 | Annoni | A61N 1/36139 |
| 2022/0287619 A1 | 9/2022 | Cleveland et al. | |

* cited by examiner

242

| | | 1ST LOCATION ON SPINAL CORD (9TH THORACIC) | 2ND LOCATION ON SPINAL CORD (8TH THORACIC) | 3RD LOCATION ON SPINAL CORD (7TH THORACIC) |
|---|---|---|---|---|
| Patient 1 (Alex) | Electric Current | 0.8 μA | 0.9 μA | 0.7 μA |
| | Noise | 0.2 mV | 0.3 mV | 0.4 mV |
| | Filtration Technique | FTT | WT | FTT |
| | SNR | 0.8 dB | 0.9 dB | 0.7 dB |
| | Correlation Coefficient | 0.81 | 0.73 | 0.85 |
| | | | | |
| Patient 2 (Frank) | Electric Current | 0.6 μA | 0.7 μA | 0.9 μA |
| | Noise | 0.3 mV | 0.2 mV | 0.3 mV |
| | Filtration Technique | WT | FTT | WT |
| | SNR | 0.6 dB | 0.7 dB | 0.9 dB |
| | Correlation Coefficient | 0.66 | 0.89 | 0.80 |
| | | | | |
| Patient 3 (Marc) | Electric Current | 0.8 μA | 0.9 μA | 0.7 μA |
| | Noise | 0.2 mV | 0.3 mV | 0.2 mV |
| | Filtration Technique | FTT | WT | FTT |
| | SNR | 0.8 dB | 0.9 dB | 0.7 dB |
| | Correlation Coefficient | 0.71 | 0.75 | 0.74 |
| | | | | |
| Patient 4 (Alice) | Electric Current | 0.7 μA | 0.9 μA | 0.6 μA |
| | Noise | 0.4 mV | 0.4 mV | 0.4 mV |
| | Filtration Technique | WT | FTT | WT |
| | SNR | 0.7 dB | 0.7 dB | 0.7 dB |
| | Correlation Coefficient | 0.89 | 0.7 | 0.76 |
| | | | | |
| Patient 5 (June) | Electric Current | 0.8 μA | 0.9 μA | 0.7 μA |
| | Noise | 0.2 mV | 0.3 mV | 0.4 mV |
| | Filtration Technique | FTT | WT | FTT |
| | SNR | 0.8 dB | 0.9 dB | 0.7 dB |
| | Correlation Coefficient | 0.77 | 0.63 | 0.78 |

FIG. 2E

SPINAL CORD STIMULATOR ELECTRODE POSITIONING SYSTEM UTILIZING AN ALGORITHM FOR FILTERING ELECTROMYOGRAPHY DATA

CROSS REFERENCE TO RELATED APPLICATIONS

The present application claims the benefit of U.S. Provisional Patent Application No. 63/175,944 filed Apr. 16, 2021 entitled "Spinal Cord Stimulator Electrode Positioning System ("SCS-EPS")," the entire disclosure of which is hereby incorporated herein by reference.

FIELD OF THE DISCLOSURE

Exemplary embodiments of the subject disclosure generally relate to a medical device in the field of neuromodulation for assisting in the placement of spinal cord stimulation electrodes, and more particularly related, to the placement of spinal cord electrodes for use in spinal cord stimulation therapy and dorsal root ganglion stimulation, utilizing an algorithm for filtering electromyography data.

BACKGROUND

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also correspond to implementations of the claimed technology.

Spinal cord stimulation (SCS) therapy is often used to deliver electrical stimulation to activate areas of a spinal cord to treat or manage chronic pain for a patient suffering from failed back surgery syndrome (FBBS) and chronic pain. Typically, SCS therapy makes use of spinal cord stimulators. The spinal cord stimulators are surgical implants used to treat FBBS and chronic pain by modifying nerve activity along the spinal cord to activate areas of the spinal cord, thereby minimizing or masking pain signals from reaching the brain of the patient. Further, SCS therapy allows a surgeon or a doctor to tailor treatment based on the patient's individual needs.

Further, SCS therapy includes two phases, the first phase is a trial phase, and the second phase is a permanent lead placement phase. It can be noted that temporary trials are placed in-office setting using lead electrodes, and the lead electrodes are placed using a small needle. The lead electrodes are further attached to an external battery. After a successful trial, SCS electrodes are placed intraoperatively by performing a small laminectomy to make space to insert and place the electrodes under fluoroscopy inside the patient's body (near the patient's spinal cord). Thus, such accurate placement of the SCS electrode impacts spinal cord stimulation treatment efficacy, and error in that can lead to a failure.

Currently, due to various complexities involved and lack of precision, the SCS electrode placement is less efficient. The SCS electrode placement has a 29% failure rate, and 34% of failures are due to inadequate pain relief. Suboptimal intraoperative electrode placement is a leading factor. Currently, there is no automated way to assess the functional placement of the SCS electrode, and even functional imaging is performed manually using specialized equipment run by a neurophysiologist with oversight. Further, the functional placement of the SCS electrode requires communication between multiple stakeholders and thus, making the SCS therapy labor-intensive, expensive, and time-consuming.

Numerous prior art exists to monitor muscle movement using electromyography (EMG), electrodes, and a control unit to send EMG data pulses out to the spinal cord. However, the prior arts do not disclose a method for extracting noiseless data from the EMG data in a real-time SCS workflow which may impact the optimized placement of the SCS electrode. Therefore, there is a need for an improved system that can facilitate filtering of the EMG data and efficient placement of spinal cord electrodes for use in spinal cord stimulation therapy and dorsal root ganglion stimulation.

SUMMARY

Various embodiments of the disclosure provide an electrode positioning system that provide for visualization of a Spinal Cord Stimulator (SCS) electrode, spinal cord midline detection, and validation of the placement of the SCS electrode relative to the spinal cord utilizing filters to filter physiological data. In accordance with an exemplary embodiment of the subject disclosure, an electrode positioning system is provided. The electrode positioning system includes a Spinal Cord Stimulation (SCS) electrode, the SCS electrode configured to apply electrical pulse currents at a contact point; a recording electrode configured to measure electrophysiologic signal triggered by the applied electrical pulse currents; an output device configured to indicate a location of the SCS electrode; and a base unit, the base unit having a data storage, an amplifier, the amplifier configured to amplify the measured electrophysiologic signal, a plurality of filters, a processor, the processor configured to: analyze the measured electrophysiologic signal, the analysis including: filtering the measured electrophysiologic signal to remove noise artifacts from the measured electrophysiologic signal, the filtering including: selecting a first filter from the plurality of filters, applying the first filter on the measured electrophysiologic signal, performing a correlation on the filtered electrophysiologic signal, the correlation including: determining a noise based on the applied filtering of the measured electrophysiologic signal; determining a Signal to Noise Ratio (SNR) based on the measured electrophysiologic signal and the determined noise, determining a correlation coefficient based on a correlation between one of the determined SNR or the filtered electrophysiologic signal with a first predetermined threshold, comparing the determined correlation coefficient to a second predetermined threshold, storing the determined correlation coefficient upon the determining that the determined correlation coefficient is above the second predetermined threshold, selecting another filter from the plurality of filters stored in the data storage, and repeating the filtering with the other filter, until the plurality of filters in the data storage is exhausted, and identify another SCS electrode location stored in the data storage; indicate a user to move the SCS electrode to the other location; and sending the filtered electrophysiologic signal to the output device.

In accordance with an aspect of the subject disclosure, the plurality of filters is a low pass filter, a high pass filter, a notch filter, Wavelet Transform (WT) filter, a Fast Fourier Transform filter, or a Short Time Fourier Transform Filter (STFT).

In accordance with another aspect of the subject disclosure, the plurality of filters is stored in a filter bank.

In accordance with still another aspect of the subject disclosure, the plurality of filters includes digital filters.

In accordance with yet another aspect of the subject disclosure, the measured electrophysiologic signal is one of an electromyography (EMG) signal or a Compound Muscle Action Potentials (CMAP).

In accordance with still another aspect of the subject disclosure, the output device comprises a display, the processor is configured to display the location of the SCS electrode relative to a spinal cord.

In accordance with yet another aspect of the subject disclosure, the processor is configured to display the filtered electrophysiologic signal.

In accordance with still another aspect of the subject disclosure, the processor is further configured to perform an electrical stimulation cycle methodology, the cycle methodology includes: generating the electrical pulse currents based on a parameter; applying the generated electrical pulse currents at the contact point; measuring electrophysiologic signals triggered by the application of the generated electrical pulse currents; comparing the measured electrophysiologic signal to a reference electrophysiologic signal; determining a deviation based on the comparison; adjusting the parameter by incrementally increasing an intensity of the electrical pulse currents, changing a pulse width, or changing a pattern of stimulus pulses upon determining that the deviation exists; repeating the generation of the electrical pulse currents, the application of the generated electrical pulse currents, the measurement of the electrophysiologic signal, the comparison of the measured electrophysiologic signal, determination of the deviation, and the adjusting of the parameter until the deviation is minimized; storing data corresponding to the contact position of the SCS electrode in which the deviation is minimized; and changing the contact position of the SCS electrode and repeating the generation of the electrical pulse currents, the application of the generated electrical pulse currents, the measurement of the electrophysiologic signal, the comparison of the measured electrophysiologic signal, the determination of the deviation, or the changing of the contact position of the SCS electrode is performed in one of a rostral-to-caudal or left to right direction.

In accordance with yet another aspect of the subject disclosure, the processor is further configured to perform a lateralization, the lateralization including: measuring a Root Mean Square (RMS) value of the stored data including the electrophysiologic signal corresponding to each of the contact positions of the SCS electrode in which the deviation is minimized; comparing the RMS value of the stored data corresponding to one of the contact points to the RMS value of the stored data corresponding to another one of the contact points; calculating a ratio between the RMS value of the stored data corresponding to the one of the contact points to the RMS value of the stored data corresponding to the other one of the contact points; designating one of the contact points as a left contact upon the ratio being less than 1; designating one of the contact points as a right contact point upon the ratio being more than 1; designating one of the contact points as a midpoint upon the ratio being 1; connecting the contacting points that are designated as the midpoint to form a midline; and outputting the midline to the output device.

In accordance with another exemplary embodiment of the subject disclosure, an electrode positioning method is provided. The electrode positioning method includes placing a Spinal Cord Stimulation (SCS) electrode on a spinal cord of a patient; using an electrode positioning system, receiving a measured electrophysiologic signal; and using the electrode positioning system, analyzing the measured electrophysiologic signal, the analysis including: filtering the measured electrophysiologic signal to remove noise artifacts from the measured electrophysiologic signal, the filtering include: selecting a first filter from a plurality of filters, applying the first filter on the measured electrophysiologic signal, performing a correlation on the filtered electrophysiologic signal, the correlation including, determining a noise based on the applied filtering of the measured electrophysiologic signal, determining a Signal to Noise Ratio (SNR) based on the measured electrophysiologic signal and the determined noise, determining a correlation coefficient based on a correlation between one of a determined SNR or the filtered electrophysiologic signal with a first predetermined threshold, comparing the determined correlation coefficient to a second predetermined threshold, storing the determined correlation coefficient upon the determining that the determined correlation coefficient is above the second predetermined threshold in the database, selecting an other filter from the plurality of filters, repeating the filtering with the selected other filter, until the plurality of filters is exhausted, identify another SCS electrode location stored in the database, and sending the filtered electrophysiologic signal to the output device.

In accordance with an aspect of the subject disclosure, the plurality of filters a low pass filter, a high pass filter, a notch filter, Wavelet Transform (WT) filter, a Fast Fourier Transform filter, or a Short Time Fourier Transform Filter (STFT).

In accordance with another aspect of the subject disclosure, the plurality of filters is stored in a filter bank.

In accordance with still another aspect of the subject disclosure, the plurality of filters includes digital circuits.

In accordance with yet another aspect of the subject disclosure, the electrophysiologic signal is an electromyography (EMG) signal and a Compound Muscle Action Potentials (CMAP).

In accordance with still another aspect of the subject disclosure, the output device comprises a display, and the method further includes displaying one of a location of a SCS electrode relative to a spinal cord on the display.

In accordance with yet another aspect of the subject disclosure, the method further includes displaying the filtered electrophysiologic signal on the display.

In accordance with still another aspect of the subject disclosure, the method further includes: performing an electrical stimulation cycle methodology, the cycle methodology including: generating electrical pulse currents based on the parameters; applying the generated electrical pulse currents at the contact point; measuring electrophysiologic signal triggered by the application of the generated electrical pulse currents; comparing the measured electrophysiologic signal to a reference electrophysiologic signal; determining a deviation based on the comparison; adjusting the parameter by incrementally increasing an intensity of the electrical pulse currents, changing a pulse width, or changing the pattern of stimulus pulses upon determining that the deviation exists; repeating the generation of the electrical pulse currents, the application of the generated electrical pulse currents, the measurement of the electrophysiologic signal, the comparison of the measured electrophysiologic signal, determination of the deviation, and the adjusting of the parameter until the deviation is minimized; storing data corresponding to the contact position of the SCS electrode in which the deviation is minimized; changing the contact position of the SCS electrode and repeating the generation of the electrical pulse currents, the application of the generated electrical pulse currents, the measurement of the electrophysiologic signal, and the comparison of the measured electrophysiologic signal, determination of the deviation, wherein the changing of the contact position of the SCS electrode is performed in one of a rostral-to-caudal, or a left to right direction.

In accordance with yet another aspect of the subject disclosure, the method further includes using the electrode positioning system of claim 1 to perform a lateralization, the lateralization including: measuring a Root Mean Square (RMS) value of the stored data including the electrophysiologic signal corresponding to each of the contact positions of the SCS electrode in which the deviation is minimized; comparing the RMS value of the stored data corresponding to one of the contact points to the RMS value of the stored data corresponding to another one of the contact points; calculating a ratio between the RMS value of the stored data corresponding to one of the contact points to the RMS of the stored data corresponding to the other one of the contact points; designating one of the contact points as a left contact upon the ratio being less than 1; designating one of the contact points as a right contact point upon the ratio being more than 1; and designating one of the contact points as a mid contact point upon the ratio being 1; connecting the contacting points that are designated as the mid contact point to form a midline; and outputting the midline to the output device.

In accordance with another exemplary embodiment of the subject disclosure, a non-transitory computer readable medium is provided. The non-transitory computer readable medium has stored thereon instructions for causing a processing circuitry configured to perform the steps of: using an electrode positioning system of claim 1, receiving a measured electrophysiologic signal; and using the electrode positioning system of claim 1, analyzing the measured electrophysiologic signal, the analysis including: filtering the measured electrophysiologic signal to remove noise artifacts from the measured electrophysiologic signal, the filtering include: selecting a first filter from a plurality of filters, applying the first filter on the measured electrophysiologic signal, performing a correlation on the filtered electrophysiologic signal, the correlation including, determining a noise based on the applied filtering of the measured electrophysiologic signal, determining a Signal to Noise Ratio (SNR) based on the measured electrophysiologic signal and the determined noise, determining a correlation coefficient based on a correlation between one of a determined SNR or the filtered electrophysiologic signal with a first predetermined threshold, comparing the determined correlation coefficient to a second predetermined threshold, storing the determined correlation coefficient upon the determining that the determined correlation coefficient is above the second predetermined threshold in the database, selecting another filter from the plurality of filters, repeating the filtering with the selected other filter, until the plurality of filters is exhausted, identify another SCS electrode location stored in the database, and sending the filtered electrophysiologic signal to the output device.

In accordance with an aspect of the subject disclosure, the processing circuitry is further configured to perform the steps of selecting another filter from the plurality of filters;

and repeating the filtering with the selected other filter, until the plurality of filters in the data bank is exhausted.

BRIEF DESCRIPTION OF THE DRAWINGS

The accompanying drawings illustrate various embodiments of systems, methods, and embodiments of various other aspects of the disclosure. Any person with ordinary skills in the art will appreciate that the illustrated element boundaries (e.g., boxes, groups of boxes, or other shapes) in the figures represent one example of the boundaries. In some examples, one element may be designed as multiple elements, or multiple elements may be designed as one. In some examples, an element shown as an internal component of one element may be implemented as an external component in another and vice versa. Furthermore, elements may not be drawn to scale. Non-limiting and non-exhaustive descriptions are described with reference to the following drawings. The components in the figures are not necessarily to scale, emphasis instead being placed upon illustrating principles.

FIG. 2E illustrates a datasheet of patient data stored in a database, according to an embodiment

DETAILED DESCRIPTION

Some embodiments of this disclosure, illustrating all its features, will now be discussed in detail. The words "comprising," "having," "containing," and "including," and other forms thereof are intended to be equivalent in meaning and be open-ended in that an item or items following any one of these words is not meant to be an exhaustive listing of such item or items, or meant to be limited to only the listed item or items.

It must also be noted that as used herein and in the appended claims, the singular forms "a," "an," and "the" include plural references unless the context dictates otherwise. Although any systems and methods similar or equivalent to those described herein can be used in the practice or testing of embodiments of the present disclosure, the preferred systems and methods are now described.

Embodiments of the present disclosure will be described more fully hereinafter with reference to the accompanying drawings in which like numerals represent like elements throughout the several figures and in which example embodiments are shown. However, embodiments of the claims may be embodied in many different forms and should not be construed as limited to the embodiments set forth herein. The examples set forth herein are non-limiting examples and are merely examples among other possible examples.

Figure 1:
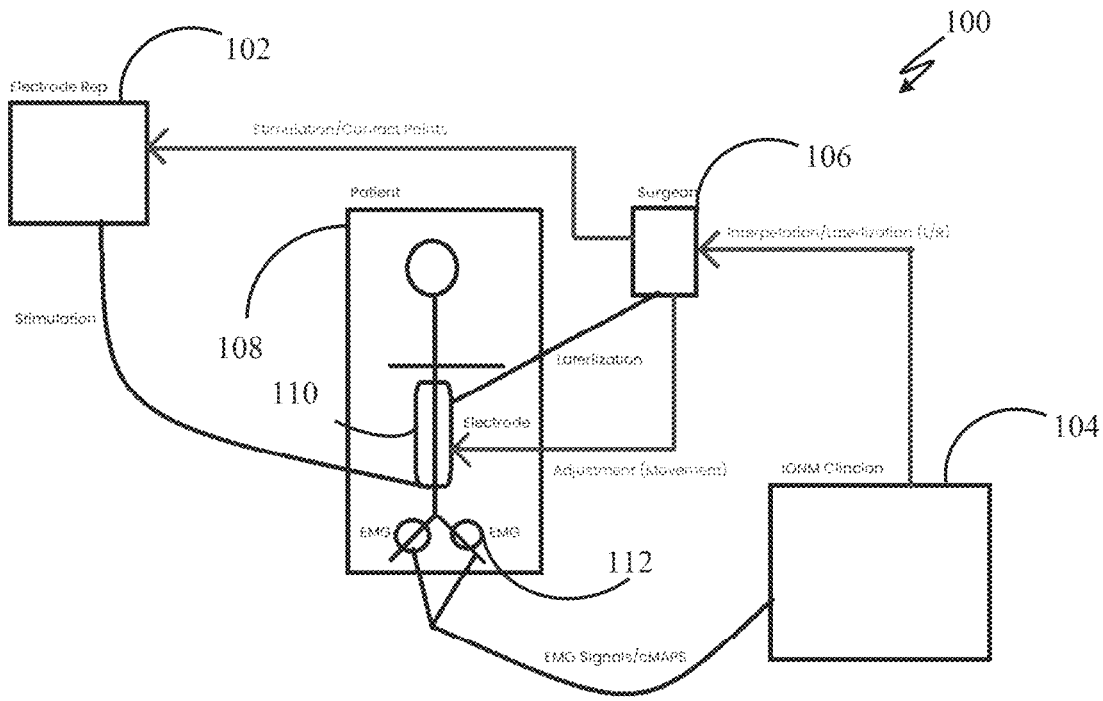
FIG. 1 illustrates a schematic diagram of a medical device system, according to an embodiment.

FIG. 1 illustrates a medical device system 100, according to an embodiment. The medical device system 100 may include an electrode representative 102, an Intraoperative Neuromonitoring (IONM) clinician 104, and a surgeon 106. It can be noted that all may be communicating with each other to treat a patient 108 by accurately placing a spinal cord stimulator (SCS) electrode 110 in the patient's body.

At first, the electrode representative 102 may control the stimulation of the SCS electrode 110 and contact points of the SCS electrode 110. In one embodiment, the SCS electrode 110 may be placed inside the patient's body, such as, but not limited to, along a dorsal column of the spinal cord of the patient 108. Successively, the stimulation of the SCS electrode 110 may generate signals to mask or mitigate pain signals from reaching the brain of the patient 108, suffering from failed back surgery syndrome (FBBS) and chronic pain, based on one or more stimulation parameters. Examples of the one or more stimulation parameters may include but are not limited to pulse width, stimulation intensity, stimulation pattern, repetition rate, and frequency. Successively, the patient's body may respond to the stimulation of the SCS electrode 110. The position of the SCS electrodes 110 may also be a stimulation parameter that can be adjusted. In an exemplary embodiment, the SCS electrode 110 may be manufactured by different manufacturers such as but not limited to Medtronic, Boston Scientific, and Abbott Laboratories. Further, the SCS electrode 110 may be either paddle electrodes or cylindrical electrodes. In the case of paddle electrodes, a laminectomy may be required to implant the paddle electrodes in the patient's body. Further, in the case of cylindrical electrodes, the patient 108 might be sedated, as the surgeon 106 slides the electrodes along the spinal cord, in a procedure requiring minimal surgical manipulation. Further, there are different types of the orientation of the SCS electrodes 110. It will be apparent to one skilled in the art that the examples mentioned above of SCS electrode 110 have been provided only for illustration purposes, without departing from the scope of the disclosure.

Further, the recording electrodes 112 attached to the patient 108 may be used to measure electromyography (EMG) activity in the patient 108 in a specific area of nerves where the SCS electrode 110 is positioned. It can be noted that the EMG activity comprises a summation of all the motor unit action potentials within the detection area of the recording electrode 112 and is used to sense isometric muscular activity related to the patient 108. Further, clinical applications of the EMG activity as a diagnostics tool can include neuromuscular diseases, back pain assessment, and disorders in motor control. In one exemplary embodiment, the recording electrodes 112 may be subdermal recording electrodes 112. In another exemplary embodiment, sticky pads may be used instead of recording electrodes 112 to measure the EMG activity. EMG data refers to any neurophysiologic data that is output by the patient 108 and measured by the recording electrodes 112, in response to the electric current output by the system 100 and applied by the SCS electrode 110. Successively, EMG signals or compound muscle action potential signals (cMAPS) may be sent to the IONM clinician 104. The IONM clinician 104 may assist the surgeon 106 with interpretation or lateralization based on the received signals. In one embodiment, interpretation may refer to a deduced meaning of the signals received from the recording electrodes 112. Further, lateralization may refer to adjusting the SCS electrode 110 placement on the patient's body. After that, the surgeon 106 may take appropriate action based on the analysis of the signals. After the clinician gives feedback on the SCS electrode 110, the surgeon can do the following things: 1—Physically move the SCS electrode 110 across the spinal cord (lateralization) to see if a better response may. 2—change which contact points on the SCS electrode 110 are being stimulated to see if a better response may be obtained. 3—ask the rep to change the stimulation parameters to acquire better signal data. In one case, the surgeon 106 may perform manual adjustment, i.e., movement of the SCS electrode 110 from one position to another position. In another case, the surgeon 106 may perform lateralization. In another case, the surgeon 106 may send the stimulation parameters or contact points to the electrode representative 102 to adjust the SCS electrode 110 in the patient's body. Stimulation parameters include adjusting the power, intensity, repetition rate of a current pattern, and frequency on the stimulating SCS electrodes 110.

Figure 2A:
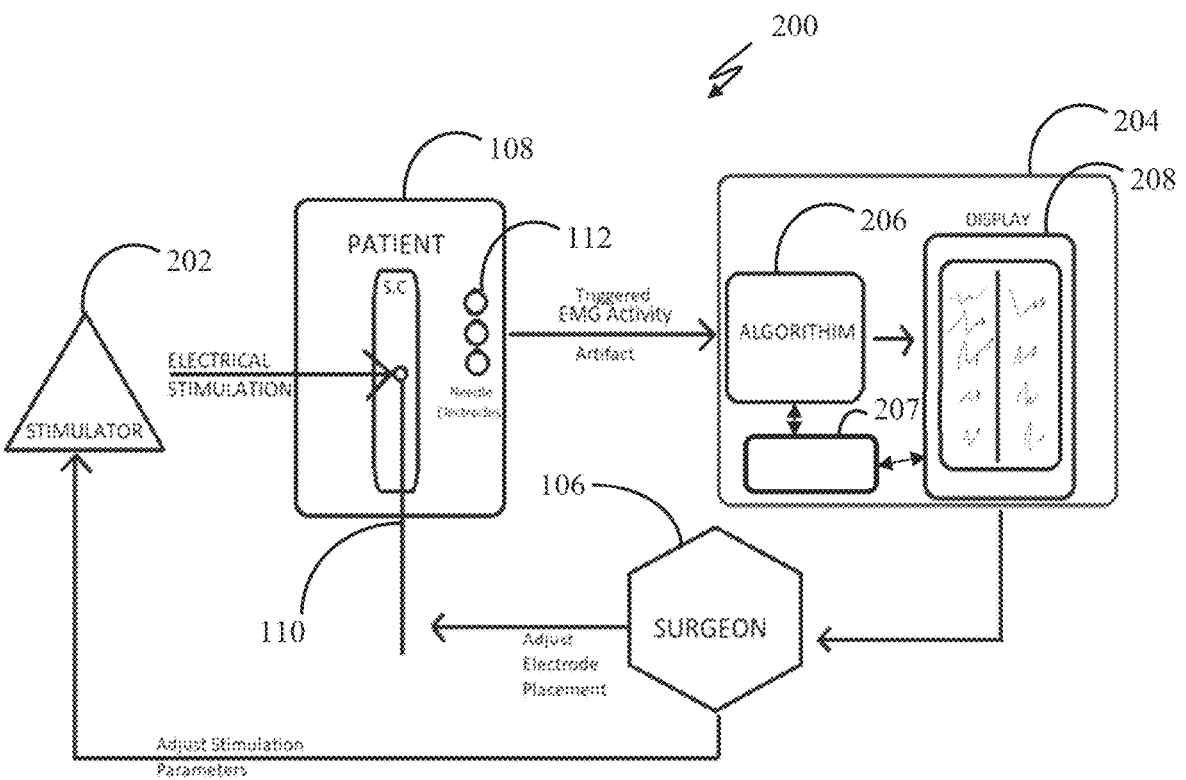
FIG. 2A illustrates a schematic diagram of a spinal cord stimulator (SCS) system to facilitate the placement of spinal cord electrodes, according to an embodiment.

FIG. 2A illustrates a schematic diagram of a spinal cord stimulator (SCS) system 200 to facilitate placement of the SCS electrode 110, according to an embodiment. It should be noted that the SCS system 200 may take input from different SCS electrodes 110. The SCS system 200 may automate functional myotomal mapping of the spinal cord to optimize the placement of the SCS electrode 110. The myotomal mapping may be achieved by an algorithm for lateralization, neuromodulation, and interpretation to optimize placement of the SCS electrode 110, wherein the algorithm for lateralization may be for placement of the SCS electrode 110 at the center of the spinal cord. Further, neuromodulation may be for modulation or adjustment of the stimulation and recording parameters by delivering electrical impulse directly to a target area, and interpretation may be for processing and visualization of placement of the SCS electrode 110.

The SCS system 200 may allow the surgeon 106 to accurately place the SCS electrode 110 inside the patient's body to maximize its effectiveness on mitigation and mediation of pain in the spinal cord of the patient 108. The SCS system 200 may be a surgeon-controlled standalone unit that guides the surgeon 106 in the placement of the SCS electrode 110 using neurophysiological data to optimize the position of the SCS electrode 110 and stimulation level for the SCS electrode 110, to optimize pain control of the patient 108. Further, the SCS system 200 may allow the surgeon 106 to easily modify and optimize stimulation and position of the SCS electrode 110 in substantially real-time without the need for additional clinical resources that are often costly and time-consuming. Further, the SCS system 200 may reduce risk by allowing the patient 108 to be placed under general anesthesia during the initial placement of the SCS electrodes 110. Such SCS system 200 may limit exposure of a patient's spinal cord during the initial placement of the SCS electrode 110 on the spinal cord.

As shown in FIG. 2A, the SCS system 200 may comprise a stimulator 202 and a base unit 204 (e.g., a device, a receiver, or an amplifier unit including an amplifier). In one embodiment, the stimulator 202 may be configured as a pulse generator. The stimulator 202 may be in communication with the SCS electrode 110. Further, the stimulator 202 may be operable to generate electrical pulses based on a variety of predetermined parameters provided by the surgeon 106 and based on the individual needs of the patient 108. In one embodiment, the predefined parameters may be referred to as stimulation parameters. The stimulation parameters may include but are not limited to pulse width, stimulation intensity, repetition rate, and frequency. The position of the SCS electrodes 110 may also be a stimulation parameter that can be adjusted. It should be noted that the electrical pulses may be used to negate and/or mitigate pain in targeted regions of the patient 108, for example, in the lower back and legs of the patient 108.

Successively, the stimulator 202 may send the electrical pulses to the SCS electrode 110 to help with myotomal mapping. Further, the recording electrodes 112 attached to the patient 108 may measure EMG data or activity in the patient 108 in a specific area of nerves where the SCS electrode 110 is positioned. Further, the EMG activity may be triggered by nerve activation resulting from electrical pulses sent to the SCS electrode 110. In one exemplary embodiment, the recording electrodes 112 may be subdermal recording electrodes 112. In another exemplary embodiment, sticky pads may be used instead of recording electrodes 112 to measure the EMG activity. Further, the SCS system 200 includes the base unit 204 that amplifies and analyzes the EMG data from the recording electrodes 112. Further, the base unit 204 may detect the type of the SCS electrode 110, based at least on different parameters such as the manufacturing company and pin configuration of the SCS electrode 110.

Further, the base unit 204 may include an algorithm module (I.e., processor programmed with application or software stored in a memory) 206 and a display device 208. In some embodiments, there may not be a separate display device 208, but rather export HDMI video information that can be y-adapted to the a fluoroscopy screen such that the animated image of the cord location identified by the algorithm module 206 can be superimposed on over the fluoroscopy screen and displayed on the display device 208 in real time. In an embodiment, the superimposed image may also be saved in data storage (i.e., memory) 207. That way, the physician simply has to look at one screen, and on it, they get a view of the bony vertebral column and the cord's location at the same time in the same image. This integration may require a reference point to ensure the two are aligned, but that is doable using a radiopaque marker in the surgical field or the electrode array itself. Waveform images may be ported to an HDMI output to another monitor in the room. If the device remains in the room between procedures, then a dedicated monitor could be set up or included as a video set that the control room manages. Electrophysiology labs, in particular, are very adept at routing tracings in this way, though for a surgical suite, some staff training may be required. The algorithm module 206 may process the EMG data using an algorithm to filter the EMG data. The EMG data is filtered to reduce the impact of artifacts generated by the stimulator 202. EMG data can also be filtered to remove any ambient noise in the room or usually introduced by other noisy equipment like OR lights, OR Bed, bear hugger, etc. It can be noted that the EMG data corresponds to real-time data. In another embodiment, the algorithm module 206 may access pre-clinical data related to the SCS electrode 110 and the recording electrodes 112. Further, the algorithm module 206 may compare the pre-clinical data to the real-time data. Based at least on the comparison of the pre-clinical data to the real-time data, the algorithm module 206 may automatically adjust the stimulation parameters and the position of the SCS electrode 110. In one embodiment, the algorithm module 206 may store the pre-clinical and real-time data in the data storage 207.

In addition, EMG activity may be measured via EMG signals in the patient's body. Further, when passing through various tissues inside the patient's body, the EMG signal may acquire various noises, artifacts, or unwanted signals. The noises may affect the quality of the EMG signal, thus causing difficulty in the analysis of the EMG signal. To overcome the noises, the EMG signal may undergo a filtration process performed by a digital filter. It can be noted that such use of a filtration process may improve the signal-to-noise ratio of the EMG signal by reducing the noise in the EMG signal. In one embodiment, the filtration process may be carried out using one filter or a combination of filters, but not limited to, low pass filter, high pass filter, and notch filter. Such filtering may maximize signal clarity and reduce the background noise of the SCS system 200 while determining an optimal threshold.

Figure 5:
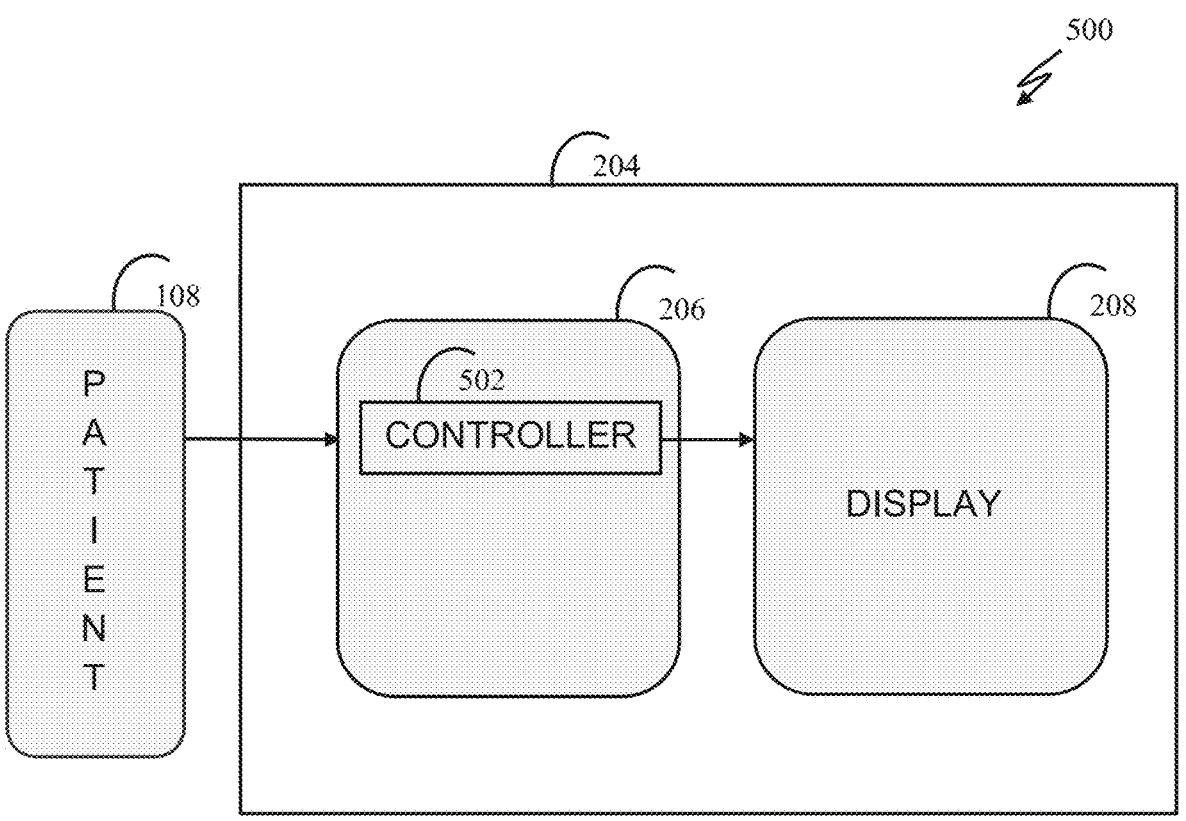
FIG. 5 illustrates a block diagram showing a setup of electromyography (EMG) data processing and displaying in the amplifier unit of the SCS system, according to an embodiment.

Further, the base unit 204 may comprise an algorithm module 206 and a display device 208. The algorithm module 206 may further comprise a controller to receive the EMG data and an algorithm to process the EMG data, as shown in FIG. 5. It can be noted that the artifacts in the EMG signal can be stimulation artifacts and M-wave. To remove the artifacts, the EMG data must be processed and may include at least, but not limited to filtering the EMG data. The EMG data is filtered to reduce the impact of artifacts generated by the stimulator 202, which may otherwise cause irregularity in the EMG data. In one exemplary embodiment, the algorithm module 206 may include performing a wavelet analysis to remove the artifacts from the received EMG data. Further, performing the wavelet analysis may include performing a wavelet transform (WT), an efficient mathematical tool that can be implemented through a discrete-time filter bank and generally used for local analysis of non-stationary and fast transient signals. The Fourier transforms of the wavelets are referred to as WT filters. The algorithm module 206 may include an Autoregressive model to process the EMG data in another exemplary embodiment. In yet another exemplary embodiment, the algorithm module 206 may include Artificial Intelligence techniques based on Neural Networks to process the EMG data.

It can be noted that the EMG data corresponds to real-time data. In another embodiment, the algorithm module 206 may access pre-clinical data related to the SCS electrode 110 and the recording electrodes 112. Further, the algorithm module 206 may compare the pre-clinical data to the real-time data. Based at least on the comparison of the pre-clinical data to the real-time data, the algorithm module 206 may automatically adjust the stimulation parameters and the position of the SCS electrode 110. In one embodiment, the algorithm module 206 may store the pre-clinical and real-time data in a database (not shown).

In another embodiment, the algorithm module 206 may display the compared data on the display device 208 for the surgeon 106. The display device 208 may be configured to display the compared data such as, but not limited to, the EMG activity, position of SCS electrode 110, the stimulation parameters related to the patient 108, to the surgeon 106. The display device 208 displays the difference in the real-time data, the pre-clinical data, and the current lateral position of the SCS electrode 110. The stimulation parameters may include but are not limited to pulse width, stimulation intensity, repetition rate, and frequency. The surgeon 106 may view the processed data so that the surgeon 106 can take the appropriate action. The action may be, but not limited to, changing the position of the SCS electrode 110, changing stimulation parameters related to the recording electrodes 112, and changing electrode type. It can be noted that such use of the algorithm module 206 may optimize the placement of the SCS electrode 110.

In one embodiment, the display device 208 may correspond to output devices including, but not limited to, video displays, graphical displays, speakers, headphones, inkjet printers, laser printers, and 3D printers. It can be noted that the function of the display device 208 may indicate to the surgeon 106 related to the EMG data. In another embodiment, the display device 208 may correspond to an input/output device like a touch screen, capable of receiving inputs from the surgeon 106, such as selecting the desired option, at the display device 208. In one embodiment, the SCS electrode 110 may be connected to the base unit 204 via an adapter, as explained in conjunction with FIG. 3.

Further, the display device 208 may be connected to an external screen or monitor to visualize the location of the SCS electrode 110, based on the EMG activity from the algorithm module 206. In one embodiment, the external screen or monitor may display the relative location of SCS electrode 110 on the spinal column based on EMG activity in real-time. The visualization of the SCS electrode 110 may vary based on the vendor and type of SCS electrode 110 utilized. Additionally, the external display may provide a visual representation of the dermatomes and/or myotomes, i.e., areas of skin/muscles, that the SCS electrode 110 is activating. It can be noted that the SCS system 200, via the display device 208, may receive feedback for positioning the SCS electrode 110 in real-time.

In another embodiment, the displayed data may be used by the surgeon 106 to adjust parameters related to the SCS electrode 110 and the location of the SCS electrode 110. In one embodiment, the parameters related to the recording electrodes 112 may be adjusted based on workflow or experience of the surgeon 106, i.e., doctor (i.e., what the doctor's experience is doing). In one embodiment, the parameters related to the recording electrodes 112 may be adjusted based on neurophysiology (i.e., needles are in the right place, but nerves don't react) or placement of the recording electrodes 112 workflows or experience of the surgeon 106. Further, the parameters related to the recording electrodes 112 may be modified manually by the surgeon 106, based upon muscle responses and data from the recording electrodes 112. In one embodiment, the algorithm module 206 may allow the surgeon 106 to manually modify stimulation parameters and position of the SCS electrode 110, based on the lateral location of the SCS electrode 110 displayed by the display device 208.

There are various scenarios of the algorithm module 206 for receiving the EMG data within the controller and processing using algorithms. In the first scenario, the algorithm module 206 may be configured to use Fast Fourier Transforms (FFT) to amplify the EMG data received from the recording electrodes 112 and display the EMG data received from the recording electrodes 112. Regarding this first scenario, in a first exemplary embodiment, the algorithm module 206 may run a simple sequence-based on convolution (signal shape) to extract signal shapes of the EMG at key frequencies. Further, the extracted EMG signal may be displayed using the displayed device 208. In a second exemplary embodiment, the EMG data may be processed using an algorithm to remove frequencies above spectra of muscle movement speeds from the EMG data.

In the second scenario, the algorithm module 206 may include algorithms to process measured artifacts and EMG activity and display the lateral location of the SCS electrode 110 in the spinal cord of the patient 108. Regarding this second scenario, in the first exemplary embodiment, an algorithm may take the EMG signal recognized, for example, through convolution and change it to metadata. In an exemplary embodiment, the metadata may include at least but not limited to a blinking light circle with no color, a blinking light circle, and a solid green circle, wherein the blinking light circle with no color may represent the SCS electrode 110 is not connected properly, a blinking light circle may represent an intermittent connection of the SCS electrode 110. and a solid green circle may represent a good stimulation by the SCS electrode 110. In a second exemplary embodiment, the display device 208 may display a blinking red signal to represent receiving a strange signal with a non-EMG signal to alert the surgeon 106.

Figure 2B:
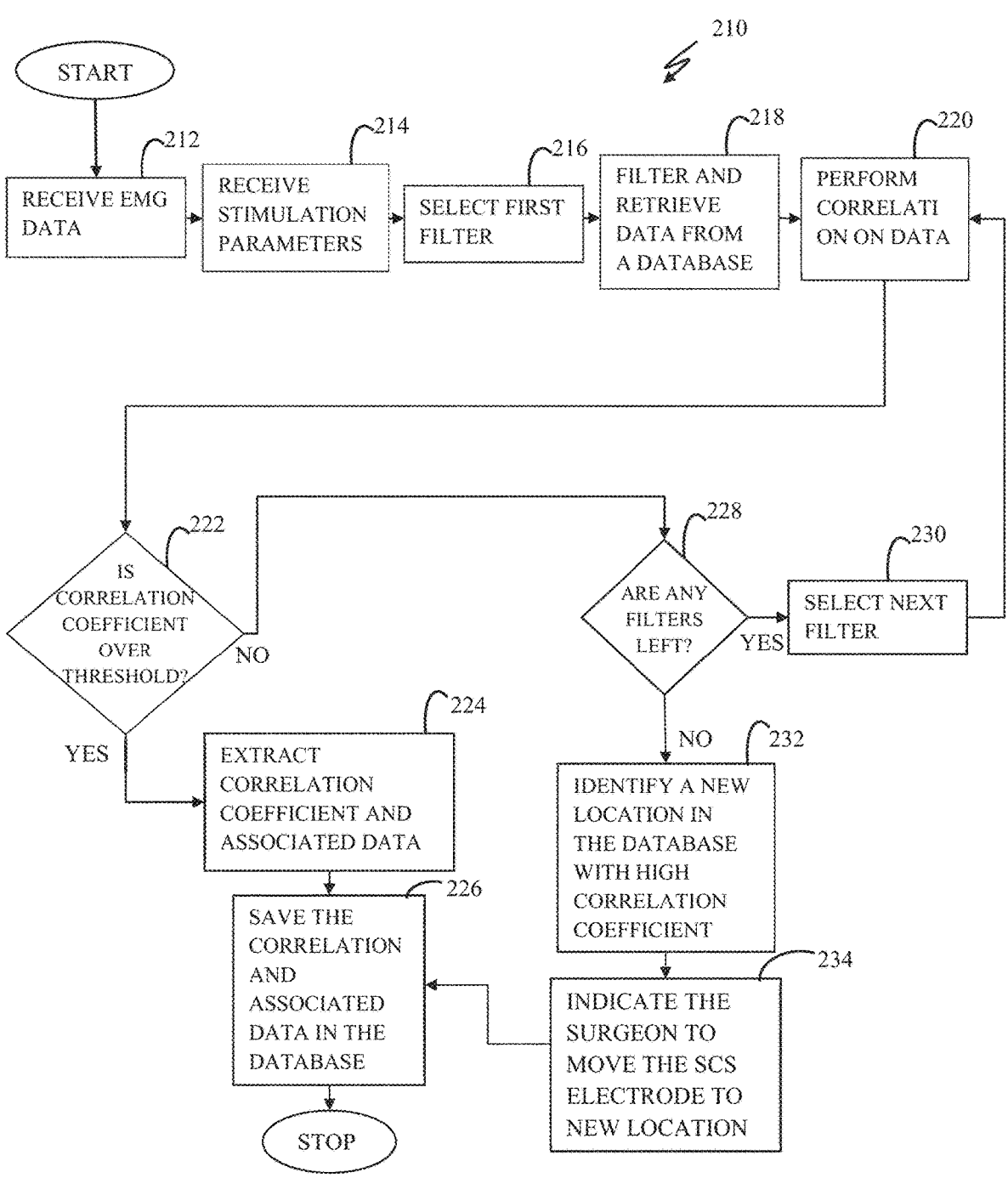
FIG. 2B illustrates a method of the algorithm module, according to an embodiment.

FIG. 2B illustrates a method 210 showing an algorithm module 206, according to an embodiment. It should also be noted that in some alternative implementations, the functions noted in the blocks may occur out of the order noted in the drawings. For example, two blocks are shown in succession in FIG. 2B may be executed substantially concurrently, or the blocks may sometimes be executed in the reverse order, depending upon the functionality involved. In addition, the process descriptions or blocks in flow charts should be understood as representing decisions made by a hardware structure such as a state machine. The flowchart 210 starts at step 212 and proceeds to step 234.

Figure 2C:
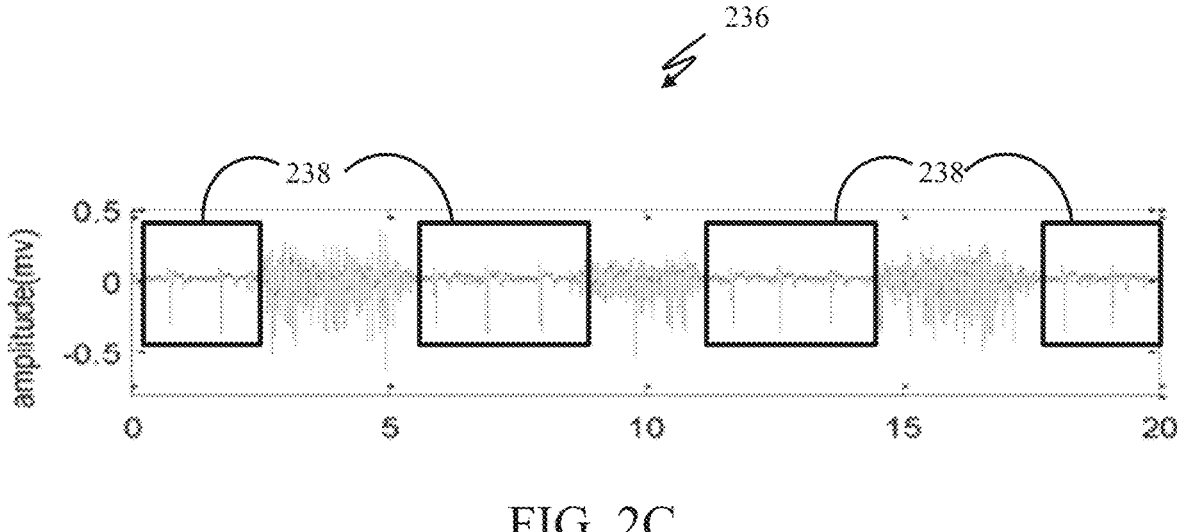
FIG. 2C illustrates a graph showing EMG activity in the presence of artifacts, according to an embodiment.

The process begins with the algorithm module 206 receives EMG data from the recording electrodes 112, at step 212. For example, Alex is suffering from back pain, and Dr. T. is operating on Alex. The SCS electrode 110 is initially implanted at the $9^{th}$ thoracic level of the spinal cord of Alex. Further, the recording electrodes 112 collect real-time data related to Alex, like EMG activity—fibrillation along with an SNR value and corresponding noise. For example, an SNR value of 0.8 dB along and a noise of 0.2 mV is received as EMG data when the SCS electrode 110 is placed at the $9^{th}$ thoracic of the spinal cord of Alex. Successively, the algorithm module 206 receives the stimulation parameters or information associated with the self-modulation of parameters associated with the SCS system 200. For example, an electric current is applied to the SCS electrode 110 at step 214. For example, an electric current of 0.8 µA is applied to the SCS electrode 110 inserted at the $9^{th}$ thoracic of the spinal cord of Alex. Successively, algorithm module 206 selects a first filter technique at step 216. For example, a filter utilizing Fast Fourier Transform (FTT) technique is selected and applied to EMG data with a noise of 0.2 mV. In one embodiment, unfiltered and filtered data is shown in FIG. 2C (with noise) and FIG. 2D (without noise, after using FTT), respectively. The algorithm module 206 filters and retrieves data from a database 242 (as shown in FIG. 2E), which may be stored in the data storage 207, related to at least one characteristic of the SCS electrode 110, at step 218. In one embodiment, the algorithm module 206 filters data associated with the location of the SCS electrode 110 or the filtering technique used to create a subset of data for a particular characteristic. Data may include patient characteristics, EMG data, stimulation parameters, or SCS electrode 110 data. For example, the algorithm module 206 filters the data based on the location of the SCS electrode 110, i.e., $9^{th}$ thoracic of the spinal cord of Alex, and the filtering technique of FTT from the database 242 shown in FIG. 2E. It can be noted that the database 242 includes information corresponding to the $9^{th}$ thoracic on the spinal cord, for different patients—Alex (electric current—0.8 μA, noise—0.2 mV, filtering technique—FTT, and SNR—0.8 dB), Frank (electric current—0.6 μA, noise—0.3 mV, filtering technique—WT, and SNR—0.6 dB), Marc (electric current—0.8 μA, noise—0.2 mV, filtering technique—FTT, and SNR—0.8 dB), Alice (electric current-0.7 μA, noise—0.4 mV, filtering technique-WT, and SNR—0.7 dB), and June (electric current—0.8 μA, noise—0.2 mV, filtering technique—FTT, and SNR—0.8 dB). Further, the subset of the filtered data includes records for electric current—0.8 μA and location as $9^{th}$ thoracic on the spinal cord.

Successively, the algorithm module 206 may perform correlations on the filtered data of the SCS electrode 110 at step 220. For example, the algorithm module 206 performs correlations between the filtered data of the SCS electrode 110 and the SNR value of 0.8 dB at $9^{th}$ thoracic of the spinal cord of Alex, based on the FTT filtering technique. The correlated data involving Alex, with the SCS electrode 110 at the $9^{th}$ thoracic of his spinal cord, has a correlation coefficient of 0.81. Further, the correlation coefficient compared with a predetermined threshold at step 222. For example, the correlation coefficient of 0.81 with the FTT filtering technique is compared with a predetermined threshold of 0.75.

If the correlation coefficient is above the predetermined threshold, the correlation coefficient is deemed highly relevant, and the correlation coefficient is extracted at step 224. For example, the correlation coefficient of 0.81 for the SCS electrode 110 placed at the $9^{th}$ thoracic of Alex's spinal cord is above the threshold of 0.75, which is extracted. After that, when it is determined that the correlation coefficient is highly relevant, then the SCS electrode 110 is at a correct location, such as in this example, the $9^{th}$ thoracic of the spinal cord of Alex. Further, the correlated coefficient is saved in the database 242 within the data storage 207, at step 226. It is assumed that some or all of the context characteristics associated with a correlation may be stored, including stimulation parameters, patient data, patient characteristics, etc. In this example, the correlation coefficient 0.81 for the SCS electrode 110 placed at the $9^{th}$ thoracic of Alex's spinal cord and the associated electric current value of 0.8 μA and the SNR value of 0.8 dB is saved in the database 350.

In another case, if the correlation coefficient is lower than the predetermined threshold at step 222, then the algorithm module 206 checks if there are any remaining filters at step 228. In one case, if there is any remaining parameter, the algorithm module 206 may select the next parameter, at step

230, to repeat steps 220 to 226. The next filter may be, but is not limited to, wavelet transform (WT) or Short Time Fourier transform (STFT). For this example, the next parameter is the WT. After that, the correlations may be performed on the rest of the filters, which are WT and STFT. It can be noted that the filters may be any filters similar to FTT, WT, and STFT without departing from the scope of the disclosure. In another case, if it is determined that there are no remaining parameters, then the algorithm module 206 a new SCS electrode 110 location from the database 242 where a relatively high correlation coefficient has been determined, at step 232. The location and the parameters may be inputted by a physician as preferred locations, or SCS electrode 110 contact points that have be pre-identified by the system 200 as triggering relatively high correlation coefficients from signals (e.g., EMG patterns) recorded by the recording electrodes 112 and pre-stored in the database 242 in the data storage 207. That is, after enough iterations of use, the system would be able to suggest SCS electrode locations based on high coefficient coefficients from patients with similar physical characteristics. The correlation coefficient threshold may also be predetermined. The desired output may be EMG patterns related to the different inputs or stimulation parameters at the same location in one embodiment. In another embodiment, the new location may be identified where inputs or stimulation parameters are correlated above a threshold with the desired output. In another embodiment, if a location is identified on the spinal cord for placing the SCS electrode 110 that connects the nerves to the location to be treated, then a variety of inputs and outputs may be correlated. The system may go through all available locations and stimulation parameters, or the physician may dictate the locations and parameters tested because there is a time constraint on the patient being sedated and the use of the operating room. After enough use, the system would be able to suggest locations based on high correlation coefficients from a cohort of similar patients. For example, based on the electric current applied by the SCS electrode 110, the resulting SNR and a high correlation coefficient of 0.85 at the $7^{th}$ thoracic of the spinal cord, relative to a predetermined threshold of 0.75 will be identified through iterative testing as described above. Successively, the identified new location may be indicated to the surgeon 106 for moving the SCS electrode 110 to the new location at step 234. For example, the $7^{th}$ thoracic of the spinal cord of Alex is indicated to Dr. T for moving the SCS electrode 110. Successively, the ML module 208 moves to step 226, to save the correlation and associated data in the database 242 and end the process.

Figure 2D:
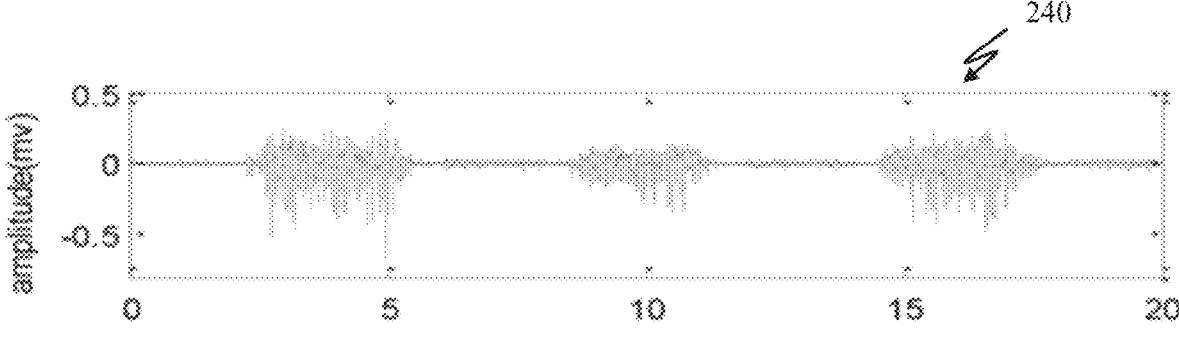
FIG. 2D illustrates a graph showing EMG activity in the absence of artifacts, after filtering artifacts, according to an embodiment.

FIG. 2C illustrates an example of unfiltered data when the SCS electrode 110 is placed at the $9^{th}$ thoracic of the spinal cord of Alex. FIG. 2C shows a graph 236 with amplitude (mV) of the output of the recording electrode 112, on the Y-axis, with respect to time on the X-axis. It can be noted that the graph 236 represents a noise component, as shown by 238. Further, FIG. 2D provides an illustration of filtered data corresponding to FIG. 2C, when the SCS electrode 110 is placed at the $9^{th}$ thoracic of the spinal cord of Alex. FIG. 2D shows a graph 240 with amplitude of the SCS electrode 110, on the Y-axis, with respect to time on the X-axis. It can be noted that the graph 240 a noiseless output of the recording electrode 112, after filtering, as explained in FIG. 2B.

Figure 3:
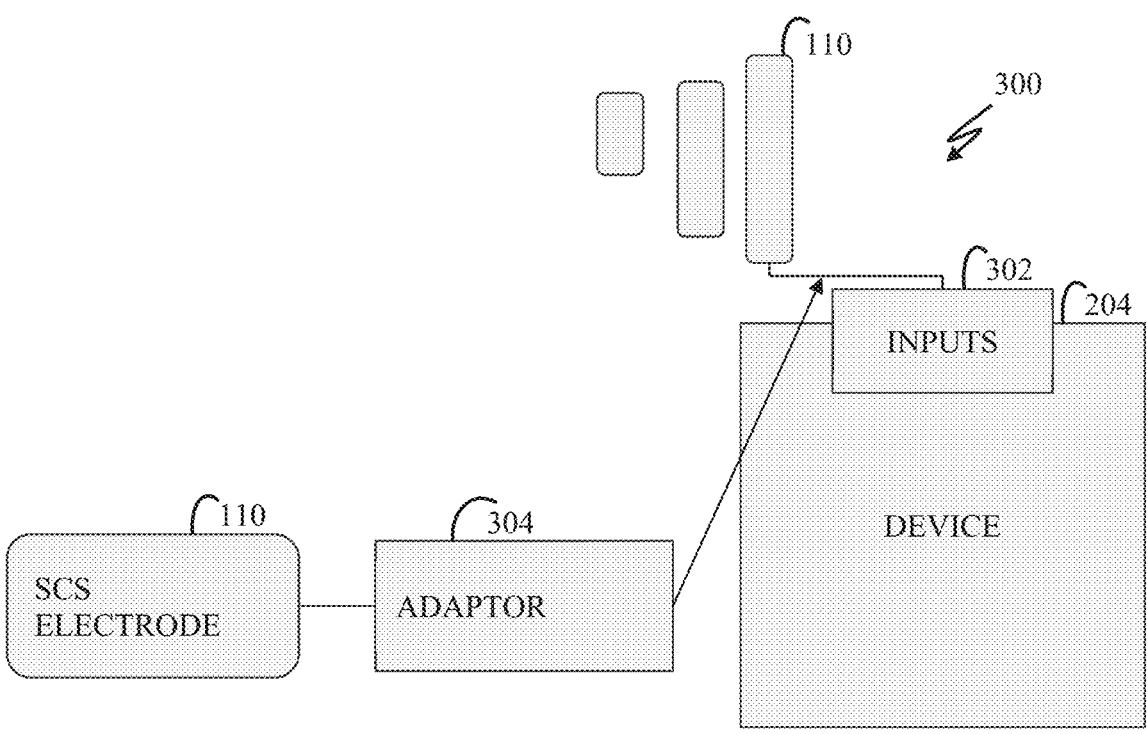
FIG. 3 illustrates the block diagram showing electrodes' connection with amplifier unit in the SCS system, using an adaptor, according to another embodiment.

FIG. 3 illustrates a block diagram 300 showing SCS electrode 110 connection with the base unit 204 in the SCS system, using an adaptor, according to an embodiment. FIG. 3 is explained in conjunction with FIG. 4A and FIG. 4B. In one embodiment, when the SCS electrode 110 is directly compatible with the base unit 204, then the SCS electrode 110 is connected directly to the base unit 204 via an input 302. In another embodiment, when the SCS electrode 110 is not directly compatible with the base unit 204, then the SCS electrode 110 is connected indirectly to the base unit 204, using an adaptor 304.

Figure 4A:
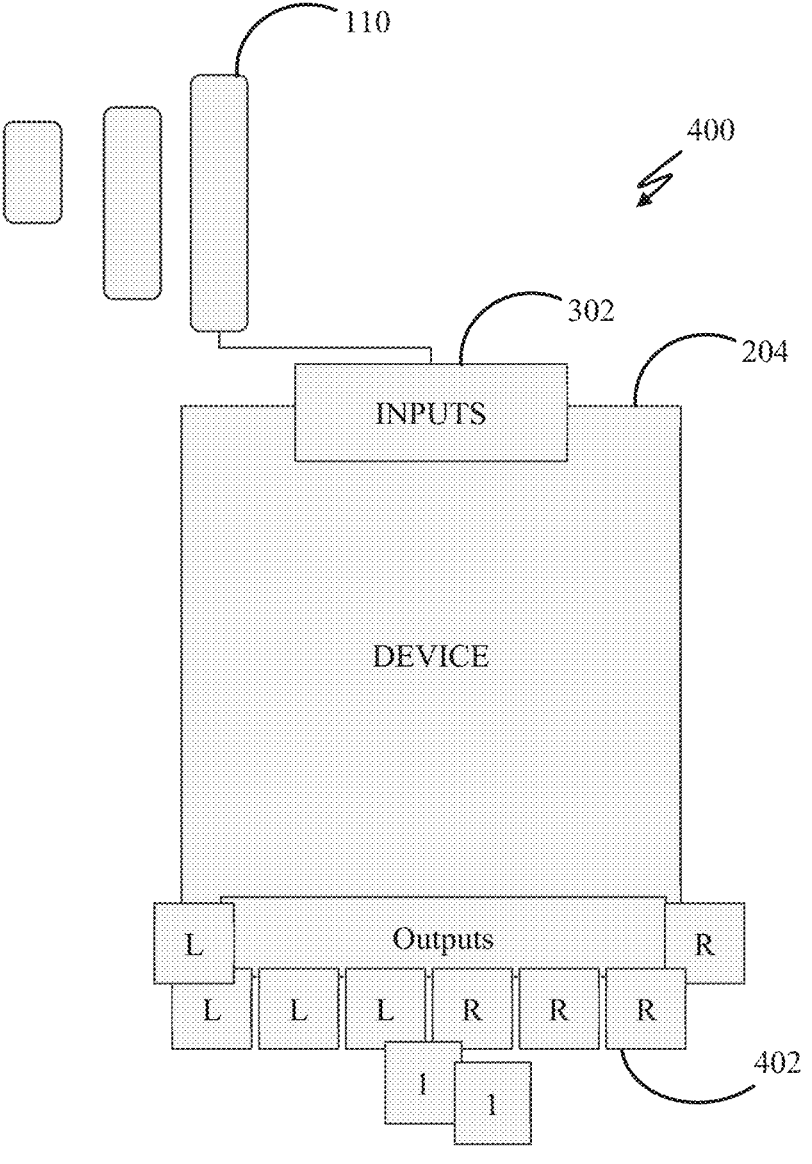
FIG. 4A illustrates a block diagram showing a connection of the SCS electrode and eight-channels machine with the amplifier unit in the SCS system, according to an embodiment.
Figure 4B:
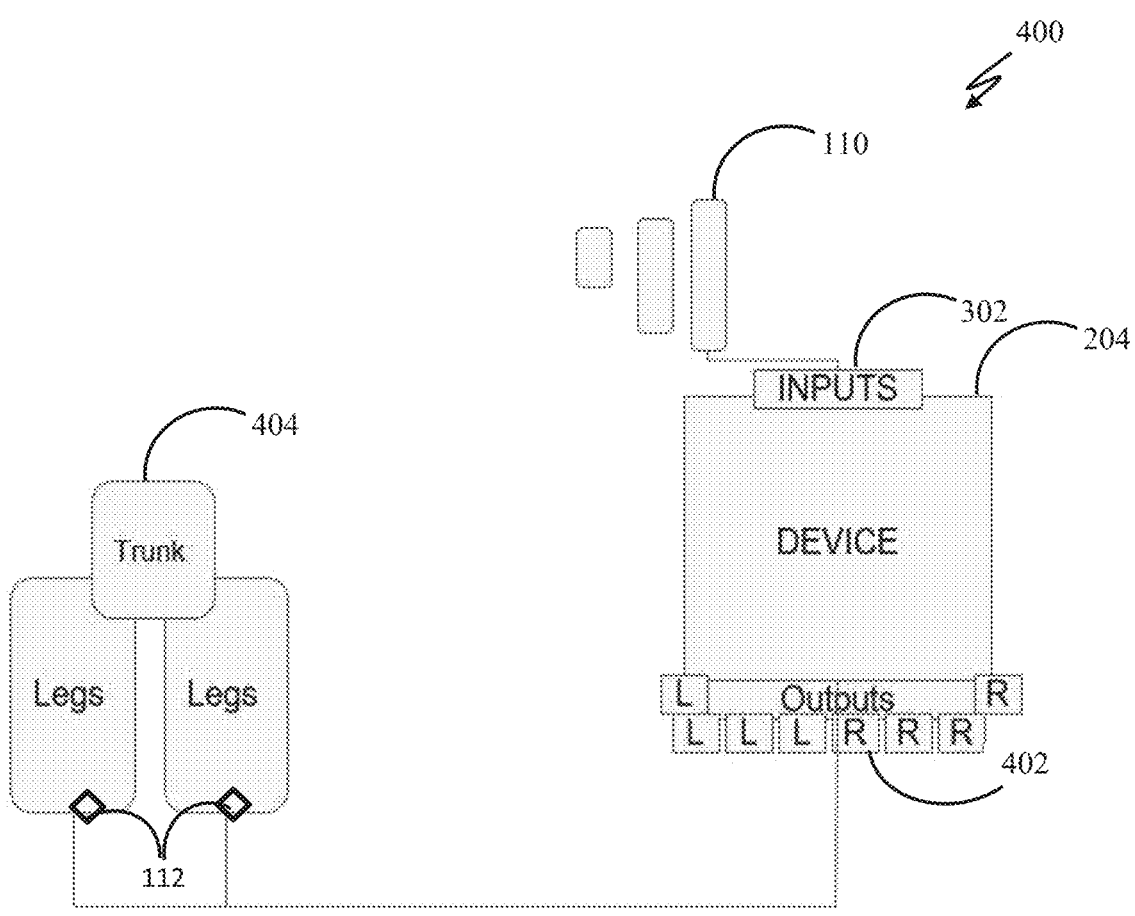
FIG. 4B illustrates a block diagram showing an exemplary scenario of the SCS system, according to an embodiment.

Further, the base unit 204 (shown as a device 204 in FIG. 4A) may be connected to the SCS electrode 110 through inputs 302 and eight-channel machine 402 through outputs to prepare the setup of the SCS system 200, as disclosed in FIG. 4A. The SCS system 200 may have the ability to take input from eight muscles of the patient's body. In one embodiment, the SCS system 200 may use a standard way of taking the EMG data through the eight-channel machine 402. It can be noted that the eight-channel machine 402 may collect one or more sensory data from the patient's body using bi-polar recordings. In one exemplary embodiment, the eight-channel machine 402 may include recording electrodes 112 having four recording electrodes 112 for left limbs and four recording electrodes 112 for right limbs of the patient 108, In one embodiment, one or more sensory data may include, but are not limited to, Bilateral PSOAS, QUAD, TA, AH, and EMG Signals. In one embodiment, the eight channels machine 402 should have the ability to take standard EMG data and appropriate amplification/hardware to read the EMG data. After connecting the SCS electrode 110 and eight channels machine 402 with the SCS system, the surgeon 106 may finalize the setup by confirming if the connections are complete and proper, as shown in FIG. 4B. in one embodiment, one end of the eight channels machine 402 may be connected to the output of the base unit 204, and the other end of eight channels machine 402 may be connected to muscles 404 of the patient 108. In one exemplary embodiment, the anesthesia may be given to the patient 108 and keep track of the degree of muscle relaxation of the patient 108 by interpreting muscle response during testing of SCS electrode 110 may be made. The muscles may be oriented on the eight channels machine in colored combinations so that each muscle may go to a predefined location. In one embodiment, the eight channels machine 402 may be connected to at least the legs and trunk of the patient 108 to take the EMG data.

Figure 6:
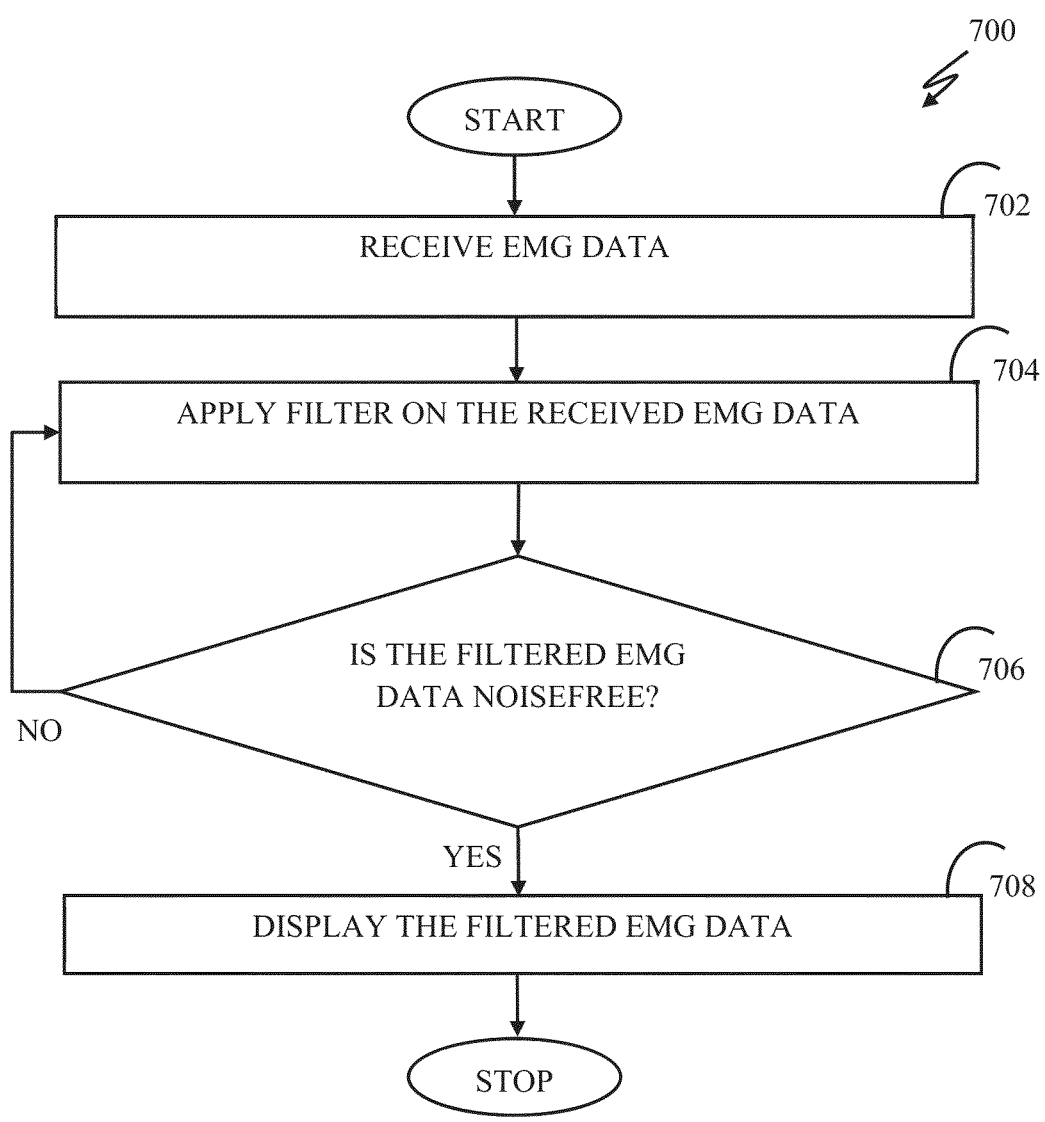
FIG. 6 illustrates a flow chart showing a methodology for filtering EMG data to extract noise-free EMG data, according to an embodiment, according to an embodiment.

The EMG data recording and displaying in the base unit 204 of the SCS system 200 is illustrated in FIG. 5, which may be explained in conjunction with FIG. 6. In FIG. 5, the base unit 204 may receive input from the patient's body. The base unit 204 may include the algorithm module 206 to receive the EMG data and the display device 208 to show the response of the EMG data. The algorithm unit 206 may further include a controller 502 to process the EMG data. In one embodiment, the controller 502 may process the EMG data using the algorithm stored in the algorithm module 206. In one embodiment, the processing of the EMG data may be to make EMG data noise-free and may be explained in conjunction with FIG. 6.

FIG. 6 illustrates a flow chart 700 showing a methodology for filtering EMG data to remove noise, as discussed in FIG. 5. In one embodiment, the noise may include at least artifacts generated by the SCS electrodes 110. In another embodiment, the noise may be other than artifacts. At first, the base unit 204 may receive the EMG data at step 702. Further, the base unit 204 may apply noise filters on the EMG data at step 704. In one embodiment, based on the frequency and amplitude of the noise, the base unit 204 may apply a set of filters to clean the EMG data. It should be noted that the algorithm applies standard filters to remove an interoperative noise. Further, the base unit 204 may also detect predefined noise profiles. The base unit 204 may detect noise profiles using artificial intelligence (AI) technology in one embodiment.

Post filtration, the base unit 204 may determine if the EMG data is noise-free at step 706. In one case, when the EMG data is noisy, the base unit 204 may again go to step 707 and apply a noise filter on the EMG data. In another case, when the EMG data is noise-free, the base unit 204 may move to step 708 and display the EMG data on the display device 208 of the base unit 204.

It can be noted that the surgeon 106 may confirm if all the connections are complete and proper. Successively, display device 208 in the base unit 204 may be activated to show the EMG data received from the SCS electrode 110.

Figure 7:
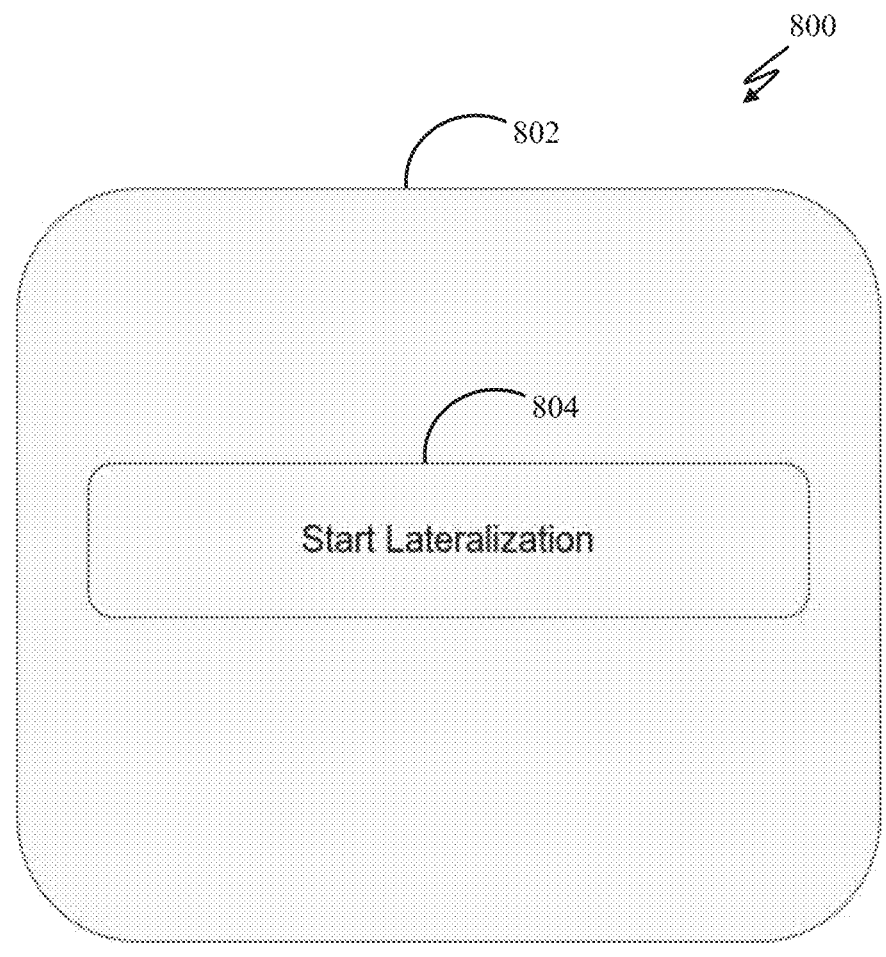
FIG. 7 illustrates a block diagram showing the UI, which facilitates the surgeon to start lateralization in the SCS system, according to an embodiment.

Further, the surgeon 106 may start lateralizing the SCS electrode 110 to position the SCS electrode 110 on the patient's body. In one embodiment, the surgeon 106 may initiate the lateralization by selecting, on a user interface (UI) 802, a start lateralization button 804, as shown in FIG. 7. Successively, the surgeon 106 may initiate the lateralization after measuring the impedances of the SCS electrode 110. The surgeon 106 may determine the SCS electrode 110 area used to stimulate, such as but not limited to "middle" or "top right" which depends on the type of SCS electrode 110 placed. In an exemplary embodiment, the type of SCS electrode 110 may vary from single column leads to multi-column paddle electrodes. In another exemplary embodiment, the SCS electrode 110 may have a bipolar configuration with a single cathode and anode. Successively, surgeon 106 may adjust SCS electrode 110 positioning to optimize left/right symmetry and/or cover localized areas of pain in the patient's body. It can be noted that data related to lateralization of the SCS electrode 110 may be represented by FIG. 8A, FIG. 8B, and FIG. 8C.

Figure 8A:
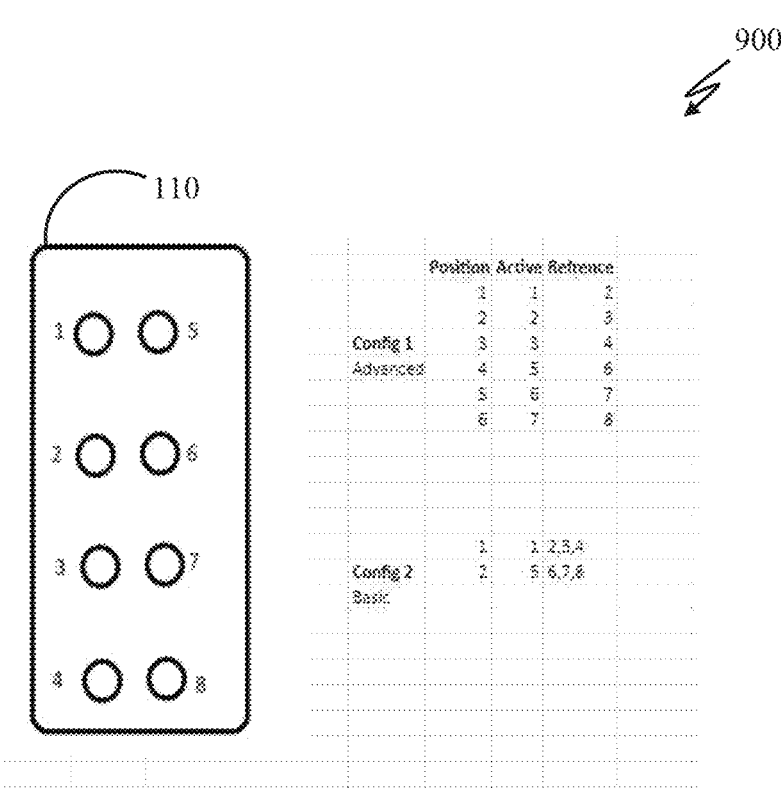
FIG. 8A illustrates a diagram showing a datasheet related to lateralization of the SCS electrode, according to an embodiment.
Figure 8B:
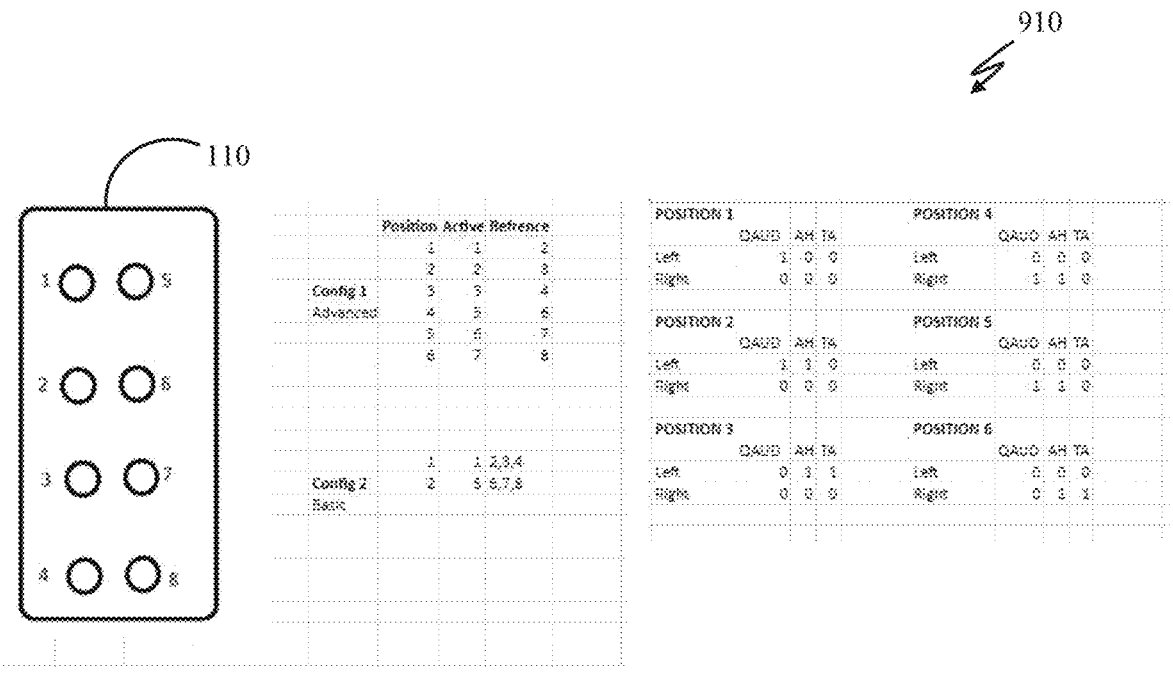
FIG. 8B illustrates a diagram showing datasheets related to lateralization of the SCS electrode, according to another embodiment.
Figure 8C:
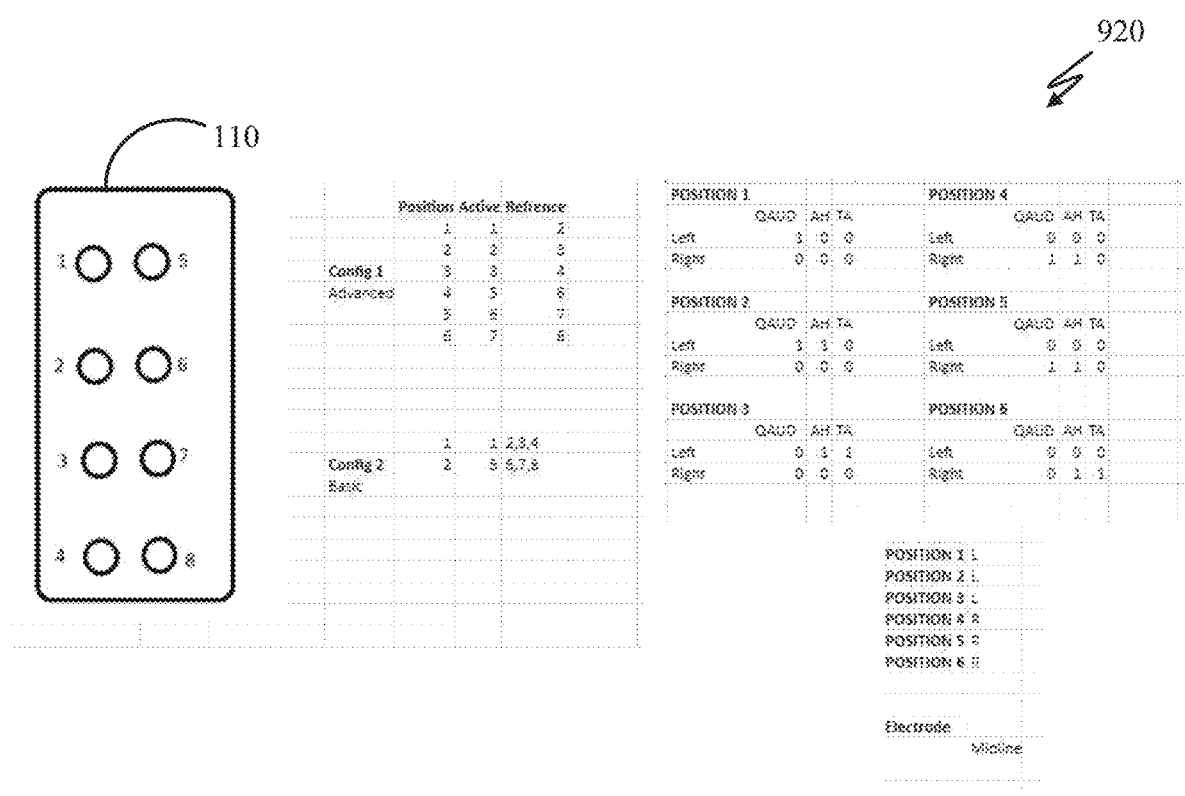
FIG. 8C illustrates a diagram showing datasheets related to lateralization of the SCS electrode, according to another embodiment.

FIG. 8A, FIG. 8B, and FIG. 8C show datasheets 900, 910, and 920, respectively, related to lateralization of the SCS electrode 110 collected and stored in the SCS system 200. The data may correspond to SCS electrode 110 positioning data. It can be noted that datasheet 900 may represent an example of SCS electrode 110 configuration data. Further, datasheet 910 may represent the EMG data after interpretation. Further, datasheet 920 may represent final data with the position of the SCS electrode 110. In an exemplary embodiment, the SCS electrode 110 is midline. Further, during pre-clinical trials, the SCS system 200 may facilitate storage and retrieval of stimulation data collected corresponding to the patient's body-specific spinal cord. Such data may include, at least but not limited to, EMG results, SCS electrode 110 positioning data, stimulation parameters, and pain-related data.

Figure 9A:
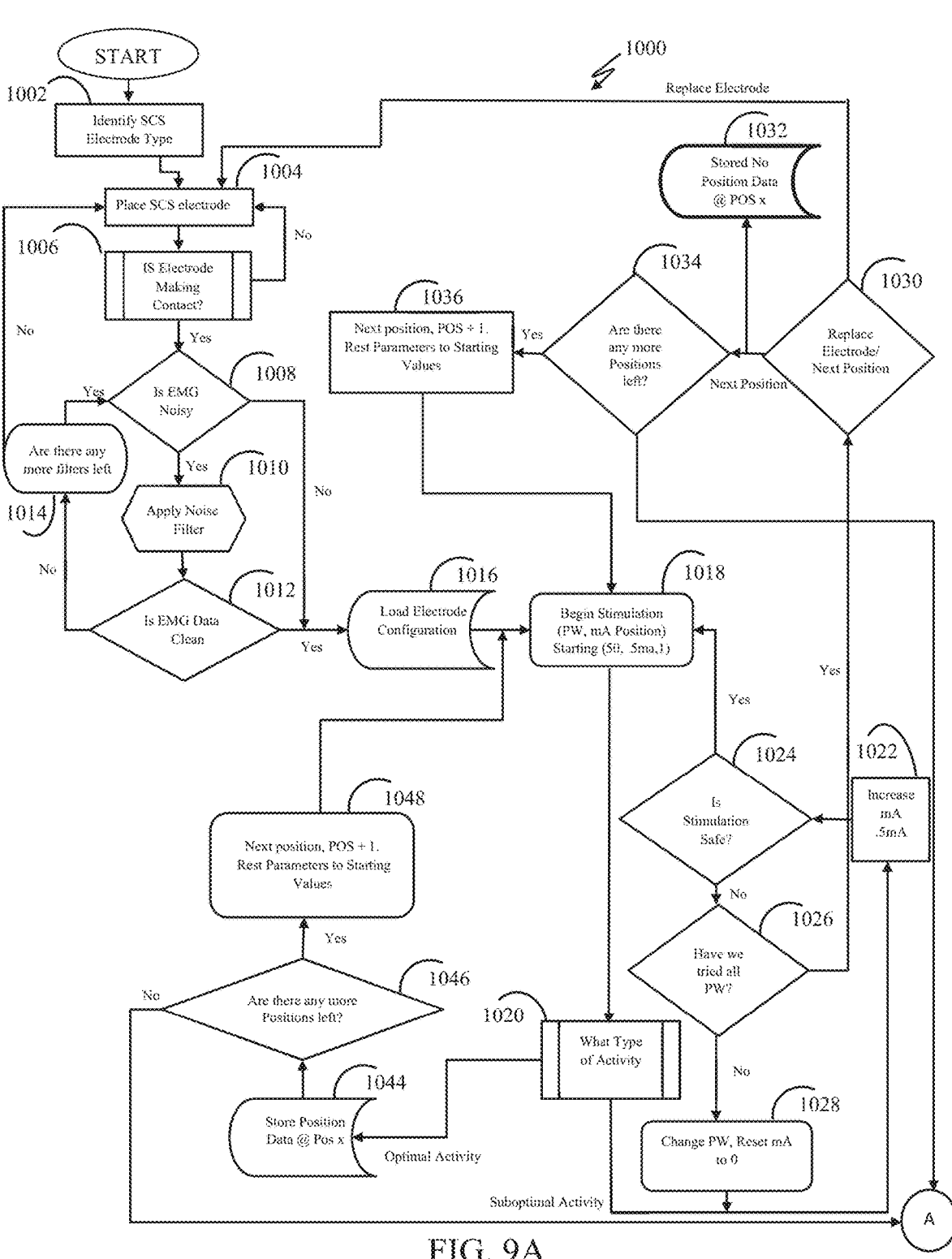
FIG. 9A illustrates a flow chart showing a method of operation of the SCS system, according to an embodiment.
Figure 9B:
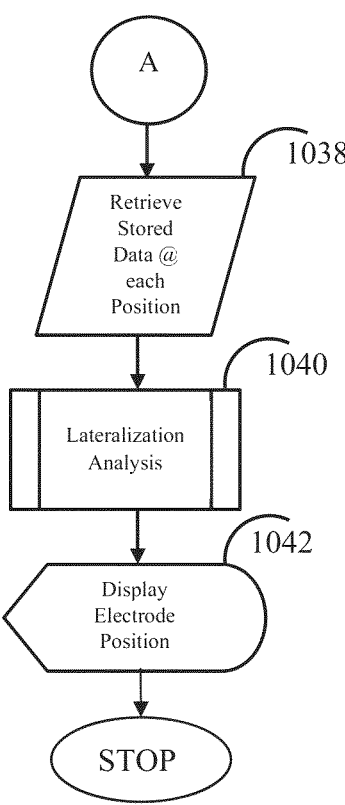
FIG. 9B illustrates a flow chart showing a method of operation of the SCS system, according to an embodiment.

The flowchart 1000 of FIGS. 9A and 9B show a method of operation of the SCS system 200, according to an embodiment. It should also be noted that in some alternative implementations, the functions noted in the blocks may occur out of the order noted in the drawings. For example, two blocks are shown in succession in FIGS. 9A and 9B may be executed substantially concurrently, or the blocks may sometimes be executed in the reverse order, depending upon the functionality involved. In addition, the process descriptions or blocks in flow charts should be understood as representing decisions made by a hardware structure such as a state machine. The flowchart 1000 starts at step 1002 and proceeds to step 1048.

At first, the SCS electrode 110 may be identified at step 1002. In one embodiment, the SCS may identify the SCS electrode 110 based on the configuration of the SCS electrode 110, such as but not limited to 2×6, 1×6, and 1×4. Post identification, the SCS electrode 110 may be placed at the spinal cord of the patient's body at step 1004. The algorithm module 206 may successfully check if the SCS electrode 110 is contacting the spinal cord at step 1006. In one case, based on the checking, if the SCS electrode 110 is not making any contact with the spinal cord, then the algorithm module 206 may execute step 1004 of placing the SCS electrode 110 at the spinal cord of the patient's body. In another case, when the SCS electrode 110 is making contact with the spinal cord, the algorithm module 206 may check if the EMG data is noisy at step 1008. When the EMG data is noisy, the algorithm module 206 may apply a noisy filter on the EMG data at step 1010. Successively, the algorithm module 206 may check if the EMG data is clean, i.e., noise-free, at step 1012. In one case, when the EMG data is still not clean based on the checking, the algorithm module 206 may check if there are any more filters left in the SCS system 200, at step 1014.

Based on the checking, if there are more filters left, the algorithm module 206 may follow steps 1008 to 1012. In another case, if there are no filters left, then the algorithm module 206 may go back to step 1004. As discussed above, at step 1008, when the EMG data is not noisy, then the algorithm module 206 may load the SCS electrode 110 configuration at step 1016. Post loading the SCS electrode 110 configuration, the algorithm module 206 may start the stimulation process at step 1018.

The stimulation may start with an initial value of pulse width, current, and position, at step 1018. In an exemplary embodiment, the initial value of pulse width is 50, the current is 0.5 ma, and the position is 1. Successively, a type of activity may be determined at step 1020. In one embodiment, the type of activity may correspond to a suboptimal activity like compound muscle action potential (cMAP). Successively, the value of current may be increased at step 1022 for a suboptimal activity. In one exemplary embodiment, the value of current is increased by 0.5 mA. After increasing the current value, the safety of stimulation may be checked to determine whether the stimulation is safe or not, at step 1024. In one case, when the stimulation is safe, then the stimulation may be started with the initial value of pulse width, current, and position, at step 1018.

In another case, when the stimulation is not safe, the SCS system 200 may check whether all pulse widths have been tried at step 1026. In one case, when all pulse widths have not been tried, then the value of the pulse width may be changed and resetting the current value to zero, at step 1028. After that, the method may follow step 1022 again to increase the value of current. In another case, when all pulse widths have been tried, then the SCS system 200 may move to the next SCS electrode 110 or indicate replacement of the SCS electrode 110, at step 1030. After placing the SCS electrode 110 in the next position, the SCS system 200 may store the position data at step 1032. Further, the SCS system 200 may check again if any more positions are left at step 1034. In one case, when there are more positions left, the SCS system 200 may change the SCS electrode 110 to the next position while keeping the rest of the parameters at an initial value at step 1036. After that, the SCS system 200 may again start the process of stimulation at step 1018. In another case, when there are no more positions left, the SCS system 200 may retrieve the stored data regarding each position of the SCS electrode 110 at step 1038. Thus, after retrieving the stored data, the algorithm module 206 may perform the lateralization at step 1040. Finally, the SCS system 200 may display the SCS electrode 110 in the UI 402 of the SCS system 200, at step 1042.

In another case, at step 1020, when the activity is determined to be an optimal activity, the SCS system 200 may store data corresponding with the position of the SCS electrode 110, at step 1044. Further, the SCS system 200 may determine if there are any more positions left for the SCS electrode 110 at step 1046. In one case, when there are positions left for the SCS electrode 110, the SCS system 200 may change the position of the SCS electrode 110 to the next position while keeping the rest of the parameters at an initial value, at step 1048. After that, the SCS system 200 may again start the process of stimulation at step 1018. In another case, when there are no more positions left, the SCS system 200 may retrieve the stored data regarding each position of the SCS electrode 110 at step 1038. Thus, after retrieving the stored data, the algorithm module 206 may perform the lateralization at step 1040. Finally, the SCS system 200 may display the SCS electrode 110 in the UI 402 of the SCS system 200, at step 1042.

The subject disclosure describes a method for using a standalone spinal cord SCS electrode 110 positioning system to visually guide the surgeon 106 in the placement of SCS electrode 110 in real-time based on a display of the position of the SCS electrode 110 on the spinal column along with corresponding filtered EMG data at said positions.

It will be appreciated by those skilled in the art that changes could be made to the exemplary embodiments described above without departing from the broad inventive concept thereof. Therefore, it is to be understood that this disclosure is not limited to the particular embodiments disclosed, but it is intended to cover modifications within the spirit and scope of the subject disclosure as disclosed above.

What is claimed is:

1. An electrode positioning system, comprising:
   a Spinal Cord Stimulation (SCS) electrode, the SCS electrode configured to apply electrical pulse currents at a contact point;
   a recording electrode configured to measure electrophysiologic signal triggered by the applied electrical pulse currents;
   an output device configured to indicate a location of the SCS electrode; and
   a base unit, the base unit having
      a data storage,
      an amplifier, the amplifier configured to amplify the measured electrophysiologic signal,
      a plurality of filters,
      a processor, the processor configured to:
         analyze the measured electrophysiologic signal, wherein analyzing the measured electrophysiologic signal includes:
            filtering the measured electrophysiologic signal to remove noise artifacts from the measured electrophysiologic signal, the filtering including:
            selecting a first filter from the plurality of filters, applying the first filter on the measured electrophysiologic signal,
            performing a correlation on the filtered electrophysiologic signal, the correlation including:
            determining a noise based on the applied filtering of the measured electrophysiologic signal;
            determining a Signal to Noise Ratio (SNR) based on the measured electrophysiologic signal and the determined noise,
            determining a correlation coefficient based on a correlation between one of the determined SNR or the filtered electrophysiologic signal with a first predetermined threshold, comparing the determined correlation coefficient to a second predetermined threshold, storing the determined correlation coefficient upon the determining that the determined correlation coefficient is above the second predetermined threshold, selecting another filter from the plurality of filters, and repeating the filtering with the another filter, until the plurality of filters is exhausted, and identify another SCS electrode location stored in a data storage, wherein identifying another SCS electrode location comprises:

classifying the SCS electrode as positioned on a first lateral side, a second lateral side, or a midpoint relative to a midline determined from electrophysiologic signals associated with the plurality of contact points of the SCS electrode, wherein the midline corresponds to a physiological midline of a subject; and selecting, as a function of classifying the SCS electrode, an alternative SCS electrode location stored in the data storage corresponding to a lateral displacement relative to a classified position of the SCS electrode;

indicate, on a user interface, a user to move the SCS electrode to the other location; and output the filtered electrophysiologic signal to the output device.

2. The electrode positioning system of claim 1, wherein the plurality of filters is a low pass filter, a high pass filter, a notch filter, Wavelet Transform (WT) filter, a Fast Fourier Transform filter, or a Short Time Fourier Transform Filter (STFT).

3. The electrode positioning system of claim 1, wherein the plurality of filters is stored in a filter bank.

4. The electrode positioning system of claim 1, wherein the plurality of filters includes digital filters.

5. The electrode positioning system of claim 1, wherein the measured electrophysiologic signal is one of an electromyography (EMG) signal or a Compound Muscle Action Potentials (CMAP).

6. The electrode positioning system of claim 1, wherein the output device comprises a display, the processor is configured to display the location of the SCS electrode relative to a spinal cord.

7. The electrode positioning system of claim 6, wherein the processor is configured to display the filtered electrophysiologic signal.

8. The electrode positioning system of claim 1, wherein the processor is further configured to perform an electrical stimulation cycle methodology, the cycle methodology includes:

generating the electrical pulse currents based on a parameter;

applying the generated electrical pulse currents at the contact point;

measuring electrophysiologic signals triggered by applying the generated electrical pulse currents;

comparing the measured electrophysiologic signal to a reference electrophysiologic signal;

determining a deviation based on comparing the measured electrophysiologic signal to the reference electrophysiologic signal;

adjusting the parameter by incrementally increasing an intensity of the electrical pulse currents, changing a pulse width, or changing a pattern of stimulus pulses upon determining that the deviation exists;

repeating an adjustment cycle including generation of the electrical pulse currents, application of the generated electrical pulse currents, measurement of the electrophysiologic signal, comparison of the measured electrophysiologic signal, determination of the deviation, and adjusting of the parameter until the deviation is minimized;

storing data corresponding to the contact position of the SCS electrode in which the deviation is minimized; and changing the contact position of the SCS electrode and repeating the generation of the electrical pulse currents, the application of the generated electrical pulse currents, the measurement of the electrophysiologic signal, the comparison of the measured electrophysiologic signal, the determination of the deviation, or the changing of the contact position of the SCS electrode is performed in one of a rostral-to-caudal or left to right direction.

9. The electrode positioning system of claim 8, wherein the processor is further configured to perform a lateralization, the lateralization including:

measuring a Root Mean Square (RMS) value of the stored data including the electrophysiologic signal corresponding to each of the contact positions of the SCS electrode in which the deviation is minimized;

comparing the RMS value of the stored data corresponding to one of the contact points to the RMS value of the stored data corresponding to another one of the contact points;

calculating a ratio between the RMS value of the stored data corresponding to the one of the contact points to the RMS value of the stored data corresponding to the other one of the contact points;

designating one of the contact points as a left contact upon the ratio being less than 1;

designating one of the contact points as a right contact point upon the ratio being more than 1;

designating one of the contact points as a midpoint upon the ratio being 1; and connecting the contacting points that are designated as the midpoint to form a midline; and outputting the midline to the output device.

10. An electrode positioning method, comprising:

placing a Spinal Cord Stimulation (SCS) electrode on a spinal cord of a patient;

measuring an electrophysiological signal trigger by an applied electrical pule current, using a recording electrode;

using an electrode positioning system, receiving the measured electrophysiologic signal; and using a processor, analyzing the measured electrophysiologic signal, wherein analyzing the measured electrophysiologic signal includes:

filtering the measured electrophysiologic signal to remove noise artifacts from the measured electrophysiologic signal, the filtering include:

selecting a first filter from a plurality of filters, applying the first filter on the measured electrophysiologic signal, performing a correlation on the filtered electrophysiologic signal, the correlation including, determining a noise based on the applied filtering of the measured electrophysiologic signal, determining a Signal to Noise Ratio (SNR) based on the measured electrophysiologic signal and the determined noise, determining a correlation coefficient based on a correlation between one of a determined SNR or the filtered electrophysiologic signal with a first predetermined threshold, comparing the determined correlation coefficient to a second predetermined threshold, storing the determined correlation coefficient upon the determining that the determined correlation coefficient is above the second predetermined threshold, selecting another filter from the plurality of filters, repeating the filtering with a selected filter, until the plurality of filters is exhausted, identifying another SCS electrode location stored in a data store, wherein identifying another SCS electrode location comprises:

classifying the SCS electrode as positioned on a first lateral side, a second lateral side, or a midpoint relative to a midline determined from electrophysiologic signals associated with a plurality of contact points of the SCS electrode, wherein the midline corresponds to a physiological midline of a subject, and selecting, as a function of classifying the SCS electrode, an alternative SCS electrode location stored in a data storage corresponding to a lateral displacement relative to a classified position of the SCS electrode, and indicating, on a user interface, to a user to move the SCS electrode to the alternative SCS electrode location, and outputting the filtered electrophysiologic signal to an output device.

11. The electrode positioning method of claim 10, wherein the plurality of filters a low pass filter, a high pass filter, a notch filter, Wavelet Transform (WT) filter, a Fast Fourier Transform filter, or a Short Time Fourier Transform Filter (STFT).

12. The electrode positioning method of claim 10, wherein the plurality of filters is stored in a filter bank.

13. The electrode positioning method of claim 10, wherein the plurality of filters includes digital circuits.

14. The electrode positioning method of claim 10, wherein the electrophysiologic signal is an electromyography (EMG) signal and a Compound Muscle Action Potentials (CMAP).

15. The electrode positioning method of claim 10, wherein the output device comprises a display, and the method further comprises displaying one of a location of the SCS electrode relative to a spinal cord on the display.

16. The electrode positioning method of claim 15, wherein the method further comprises displaying the filtered electrophysiologic signal on the display.

17. The electrode positioning method of claim 10, further comprising performing an electrical stimulation cycle methodology, the cycle methodology including:

generating electrical pulse currents based on a parameter;

applying the generated electrical pulse currents at the contact point;

measuring electrophysiologic signal triggered by applying the generated electrical pulse currents;

comparing the measured electrophysiologic signal to a reference electrophysiologic signal;

determining a deviation based on comparing the measured electrophysiologic signal to the reference electrophysiologic signal;

adjusting the parameter by incrementally increasing an intensity of the electrical pulse currents, changing a pulse width, or changing a pattern of stimulus pulses upon determining that the deviation exists;

repeating an adjustment cycle including generation of the electrical pulse currents, application of the generated electrical pulse currents, measurement of the electrophysiologic signal, comparison of the measured electrophysiologic signal, determination of the deviation, and adjusting of the parameter until the deviation is minimized;

storing data corresponding to the contact position of the SCS electrode in which the deviation is minimized; and changing the contact position of the SCS electrode and repeating the generation of the electrical pulse currents, the application of the generated electrical pulse currents, the measurement of the electrophysiologic signal, and the comparison of the measured electrophysiologic signal, determination of the deviation, wherein the changing of the contact position of the SCS electrode is performed in one of a rostral-to-caudal, or a left to right direction.

18. The electrode positioning method of claim 17, further comprising:

using the electrode positioning system of claim 1 to perform a lateralization, the lateralization including:

measuring a Root Mean Square (RMS) value of the stored data including the electrophysiologic signal corresponding to each of the contact positions of the SCS electrode in which the deviation is minimized;

comparing the RMS value of the stored data corresponding to one of the contact points to the RMS value of the stored data corresponding to another one of the contact points;

calculating a ratio between the RMS value of the stored data corresponding to one of the contact points to the RMS of the stored data corresponding to another one of the contact points;

designating one of the contact points as a left contact upon the ratio being less than 1;

designating one of the contact points as a right contact point upon the ratio being more than 1; and designating one of the contact points as a mid contact point upon the ratio being 1;

connecting the contacting points that are designated as the mid contact point to form a midline; and outputting the midline to the output device.

19. A non-transitory computer readable medium having stored thereon instructions for causing a processing circuitry configured to perform steps of:

using an electrode positioning system of claim 1, receiving a measured electrophysiologic signal; and using an electrode positioning system, analyzing the measured electrophysiologic signal, wherein analyzing the measured electrophysiologic signal includes:

filtering the measured electrophysiologic signal to remove noise artifacts from the measured electrophysiologic signal, the filtering include:

selecting a first filter from a plurality of filters, applying the first filter on the measured electrophysiologic signal, performing a correlation on the filtered electrophysiologic signal, the correlation including, determining a noise based on the applied filtering of the measured electrophysiologic signal, determining a Signal to Noise Ratio (SNR) based on the measured electrophysiologic signal and the determined noise, determining a correlation coefficient based on a correlation between one of a determined SNR or the filtered electrophysiologic signal with a first predetermined threshold, comparing the determined correlation coefficient to a second predetermined threshold, storing the determined correlation coefficient upon the determining that the determined correlation coefficient is above the second predetermined threshold in a database, selecting another filter from the plurality of filters, repeating the filtering with the selected other filter, until the plurality of filters is exhausted, and identifying another SCS electrode location stored in the database, wherein identifying another SCS electrode location comprises:

classifying the SCS electrode as positioned on a first lateral side, a second lateral side, or a midpoint relative to a midline determined from electrophysiologic signals associated with the plurality of contact points of the SCS electrode, wherein the midline corresponds to a physiological midline of a subject, and selecting, as a function of classifying the SCS electrode, an alternative SCS electrode location stored in the data storage corresponding to a lateral displacement relative to a classified position of the SCS electrode, and outputting the filtered electrophysiologic signal to the output device.

\* \* \* \* \*